(12) United States Patent
Hagadorn et al.

(10) Patent No.: US 7,973,116 B2
(45) Date of Patent: Jul. 5, 2011

(54) PYRIDYLDIAMIDO TRANSITION METAL COMPLEXES, PRODUCTION AND USE THEREOF

(75) Inventors: John R. Hagadorn, Houston, TX (US); Catherine Anne Faler, Houston, TX (US); Timothy M. Boller, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/180,132

(22) Filed: Jul. 25, 2008

(65) Prior Publication Data

US 2010/0022726 A1 Jan. 28, 2010

(51) Int. Cl.
*C08F 4/52* (2006.01)
(52) U.S. Cl. ...................................................... 526/172
(58) Field of Classification Search .................... 526/172
See application file for complete search history.

(56) References Cited

U.S. PATENT DOCUMENTS

| | | | |
|---|---|---|---|
| 5,318,935 | A | 6/1994 | Canich et al. |
| 6,103,657 | A | 8/2000 | Murray |
| 6,521,793 | B1 | 2/2003 | Guram et al. |
| 6,750,345 | B2 | 6/2004 | Boussie et al. |
| 6,900,321 | B2 | 5/2005 | Boussie et al. |
| 7,018,949 | B2 | 3/2006 | Boussie et al. |
| 7,041,765 | B2 | 5/2006 | Tau et al. |
| 7,045,583 | B2 | 5/2006 | Kuchta et al. |
| 7,102,006 | B2 | 9/2006 | Vogel et al. |
| 7,164,020 | B2 | 1/2007 | Vogel |
| 2004/0220050 | A1 | 11/2004 | Frazier et al. |

FOREIGN PATENT DOCUMENTS

| | | | |
|---|---|---|---|
| JP | 2001048925 | * | 2/2001 |
| WO | WO 2005/095469 | | 10/2005 |
| WO | WO 2007/067965 | | 6/2007 |

OTHER PUBLICATIONS

Froese et al., Mechanism of Activation of a Hafnium Pyridyl-Amide Olefin Polymerization Catalyst: Ligand Modification by Monomer, J. Am. Chem. Soc., 2007, vol. 129, No. 25, pp. 7831-7840.
Guérin et al., Synthesis, Structure, and Reactivity of Zirconium Alkyl Complexes Bearing Ancillary Pyridine Diamide Ligands, Organometallics, 1998, vol. 17, No. 23, pp. 5172-5177.

* cited by examiner

*Primary Examiner* — Ling-Siu Choi
*Assistant Examiner* — Sonya Wright

(57) ABSTRACT

Pyridyldiamido transition metal complexes are disclosed for use in alkene polymerization. The ligands are tridentate with an NNN configuration. The general formula is:

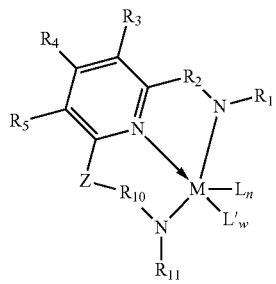

where M, Z, $L_n$, $L_w'$, $R^1$-$R^5$, $R^{10}$ and $R^{11}$ are as defined in the specification.

20 Claims, 2 Drawing Sheets

Figure 1. Molecular structure of complex C3·Et₂O
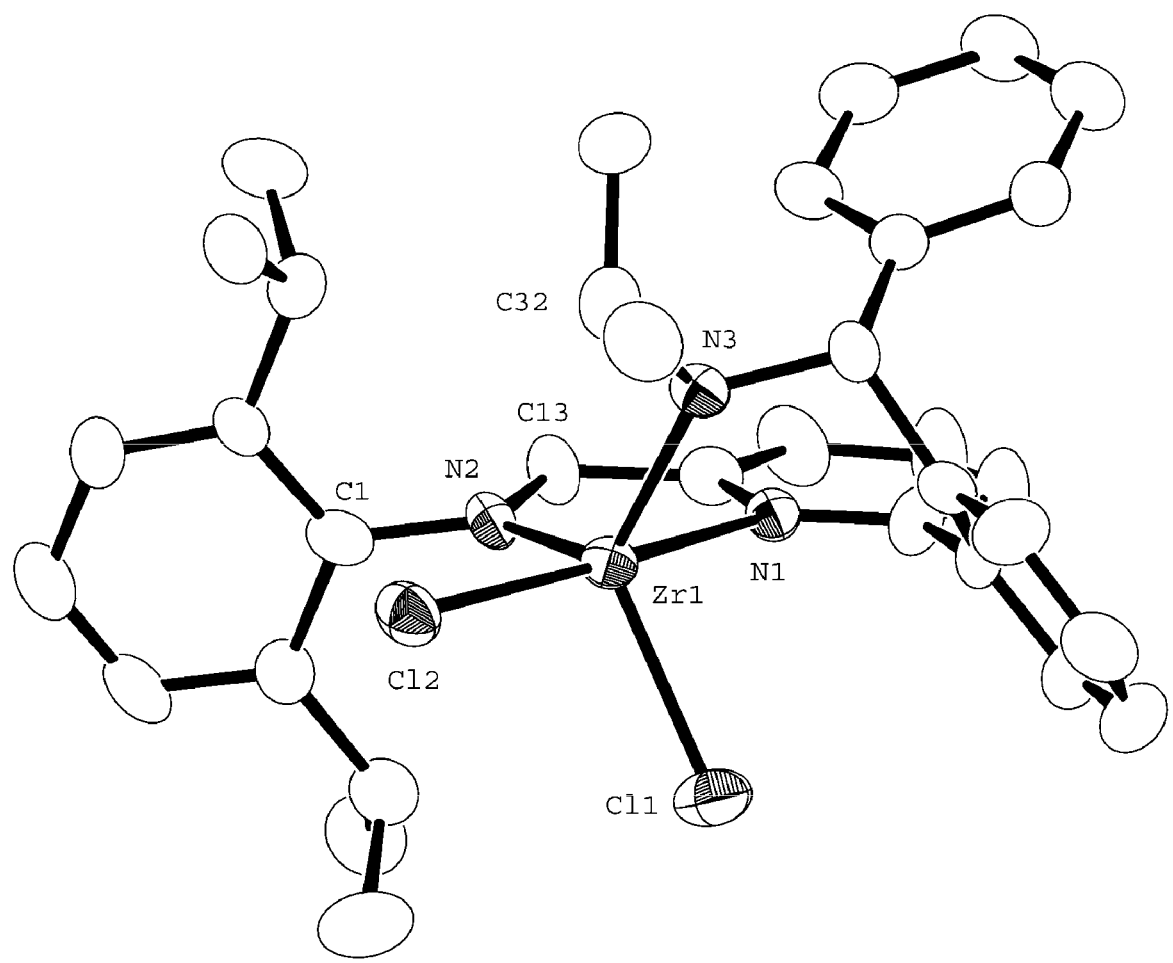

Figure 2. Molecular structure of complex C7 hexane.
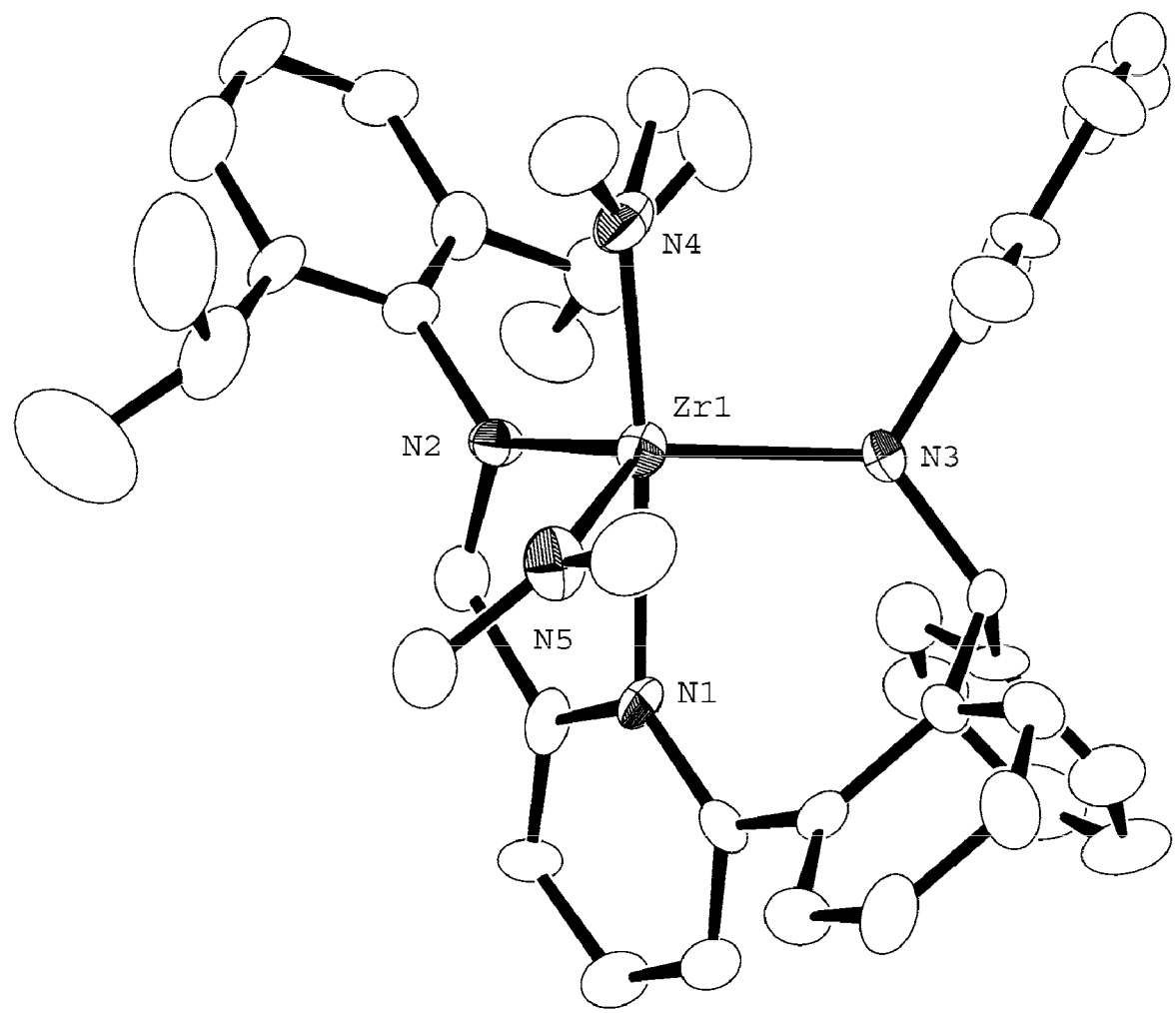

PYRIDYLDIAMIDO TRANSITION METAL COMPLEXES, PRODUCTION AND USE THEREOF

FIELD OF INVENTION

The invention relates to pyridyldiamido transition metal complexes and intermediates and processes especially but not exclusively for use in making such pyridyldiamido complexes. The transition metal complexes may be used as catalysts for alkene polymerization processes.

BACKGROUND OF INVENTION

Pyridyl amines have been used to prepare Group 4 complexes which are useful transition metal components for use in the polymerization of alkenes, see for example US 2002/0142912, U.S. Pat. No. 6,900,321, and U.S. Pat. No. 6,103,657, where the ligands have been used in complexes in which the ligands are coordinated in a bidentate fashion to the transition metal atom.

WO 2005/095469 shows catalyst compounds that use tridentate ligands through two nitrogen atoms (one amido and one pyridyl) and one oxygen atom.

US 2004/0220050A1 and WO 2007/067965 disclose complexes in which the ligand is coordinated in a tridentate fashion through two nitrogen (one amido and one pyridyl) and one carbon (aryl anion) donors.

A key step in the activation of these complexes is the insertion of an alkene into the metal-aryl bond of the catalyst precursor (Froese, R. D. J. et al., J. Am. Chem. Soc. 2007, 129, 7831-7840) to form an active catalyst that has both five-membered and a seven-membered chelate rings.

There still is need for adding synthetic routes to widen the range of catalysts complexes that may be prepared and broaden their performance in alkene polymerization. The performance may be varied in respect of the amount of polymer produced per amount of catalyst (generally referred to as the "activity") under the prevailing polymerization conditions; the molecular weight and molecular weight distribution achieved at a given temperature; and the placement of higher alpha-olefins in terms of the degree of stereoregular placement.

SUMMARY OF INVENTION

This invention relates to novel transition metal complexes having tridentate NNN ligands. The ligand may be derived from a neutral ligand precursor or be created in situ in a complex, as will be described. This invention also relates to a pyridyldiamido transition metal complex having the general formula: (I)

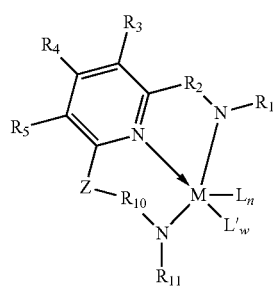

wherein:
M is a Group 3, 4, 5, 6, 7, 8, 9, 10, 11 or 12 metal;
Z is

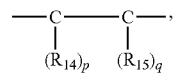

where $R_{14}$ and $R_{15}$ are independently selected from the group consisting of hydrogen, hydrocarbyls (preferably alkyls), and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings,
p is 1 or 2, and
q is 1 or 2;
$R_1$ and $R_{11}$ are independently selected from the group consisting of hydrocarbyls (such as alkyls, aryls), substituted hydrocarbyls (such as heteroaryls), and silyl groups;
$R_2$ and $R_{10}$ are each, independently, $-E(R_{12})(R_{13})-$ with E being carbon, silicon, or germanium, and each $R_{12}$ and $R_{13}$ being independently selected from the group consisting of hydrogen, hydrocarbyls (e.g. alkyl and aryl), substituted hydrocarbyls (e.g. heteroaryl), alkoxy, silyl, amino, aryloxy, halogen, and phosphino, $R_{12}$ and $R_{13}$ may be joined to form a saturated, substituted or unsubstituted hydrocarbyl ring, where the ring has 4, 5, 6, or 7 ring carbon atoms and where substitutions on the ring can join to form additional rings, or $R_{12}$ and $R_{13}$ may be joined to form a saturated heterocyclic ring, or a saturated substituted heterocyclic ring where substitutions on the ring can join to form additional rings;
$R_3$, $R_4$, and $R_5$ are independently selected from the group consisting of hydrogen, hydrocarbyls (e.g. alkyls and aryls), substituted hydrocarbyls (e.g. heteroaryl), alkoxy, aryloxy, halogen, amino, and silyl, and wherein adjacent R groups ($R_3$ & $R_4$, and/or $R_4$ & $R_5$) may be joined to form a substituted or unsubstituted hydrocarbyl or heterocyclic ring, where the ring has 5, 6, 7, or 8 ring atoms and where substitutions on the ring can join to form additional rings;
L is an anionic leaving group, where the L groups may be the same or different and any two L groups may be linked to form a dianionic leaving group;
n is 0, 1, 2, 3, or 4;
L' is neutral Lewis base; and
w is 0, 1, 2, 3 or 4.

This invention further relates to process to make the above complex, process to make intermediates for the above complex and methods to polymerize olefins using the above complex.

BRIEF DESCRIPTION OF THE DRAWINGS

FIG. 1 is an illustration of the molecular structure of transition metal complex C3 according to the invention as determined by single-crystal X-ray diffraction, and drawn with 50% thermal ellipsoids. Cocrystallized ether molecules and hydrogens are omitted for clarity.

FIG. 2 is an illustration of the molecular structure of transition metal complex C7 according to the invention as determined by single-crystal X-ray diffraction and drawn with 30% thermal ellipsoids. Cocrystallized hexane molecules and hydrogens are omitted for clarity.

DETAILED DESCRIPTION

The specification describes transition metal complexes. The term complex is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator which is believed to create a cation as a result of the removal of an anionic group, often referred to as a leaving group, from the transition metal.

As used herein, the numbering scheme for the Periodic Table groups is the new notation as set out in Chemical and Engineering News, 63(5), 27 (1985).

As used herein, Me is methyl, Et is ethyl, t-Bu and $^t$Bu are tertiary butyl, iPr and $^i$Pr are isopropyl, Cy is cyclohexyl, THF (also referred to as thf) is tetrahydrofuran, Bn is benzyl, and Ph is phenyl.

The term "substituted" means that a hydrogen has been replaced with a heteroatom or a hydrocarbyl group. For example methyl-cyclopentadiene is substituted with a methyl group.

The terms "hydrocarbyl radical," "hydrocarbyl" and "hydrocarbyl group" are used interchangeably throughout this document. Likewise the terms "group", "radical", and "substituent" are also used interchangeably in this document. For purposes of this disclosure, "hydrocarbyl radical" is defined to be $C_1$-$C_{100}$ radicals, that may be linear, branched, or cyclic, and when cyclic, aromatic or non-aromatic.

Substituted hydrocarbyl radicals are radicals in which at least one hydrogen atom of the hydrocarbyl radical has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like, or where at least one heteroatom has been inserted within a hydrocarbyl ring.

The term "catalyst system" is defined to mean a complex/activator pair. When "catalyst system" is used to describe such a pair before activation, it means the unactivated catalyst complex (precatalyst) together with an activator and, optionally, a co-activator. When it is used to describe such a pair after activation, it means the activated complex and the activator or other charge-balancing moiety. The transition metal compound may be neutral as in a precatalyst, or a charged species with a counter ion as in an activated catalyst system.

Complex, as used herein, is also often referred to as catalyst precursor, precatalyst, catalyst, catalyst compound, transition metal compound, or transition metal complex. These words are used interchangeably. Activator and cocatalyst are also used interchangeably.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound.

Noncoordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator, and stoichiometric ionic activator can be used interchangeably. Likewise, the terms neutral stoichiometric activator, and Lewis acid activator can be used interchangeably. The term non-coordinating anion includes neutral stoichiometric activators, ionic stoichiometric activators, ionic activators, and Lewis acid activators.

When a polymer or oligomer is referred to as comprising an olefin, the olefin present in the polymer or oligomer is the polymerized or oligomerized form of the olefin. An oligomer is defined to be compositions having 2-50 monomer units. A polymer is defined to be compositions having 51 or more monomer units.

A higher α-olefin is defined to be an α-olefin having 4 or more carbon atoms.

Unless otherwise noted, all molecular weights units (e.g., Mw, Mn, Mz) are g/mol.

Unless otherwise noted all melting points ($T_m$) are DSC second melt.

A "ring carbon atom" is a carbon atom that is part of a cyclic ring structure. By this definition, a benzyl group has six ring carbon atoms and para-methylstyrene also has six ring carbon atoms.

The term "aryl" or "aryl group" means a six carbon aromatic ring and the substituted variants thereof, including but not limited to, phenyl, 2-methyl-phenyl, xylyl, 4-bromo-xylyl. Likewise heteroaryl means an aryl group where a ring carbon atom (or two or three ring carbon atoms) has been replaced with a heteroatom, preferably N, O, or S.

The term "ring atom" means an atom that is part of a cyclic ring structure. By this definition, a benzyl group has six ring atoms and tetrahydrofuran has 5 ring atoms.

A heterocyclic ring is a ring having a heteroatom in the ring structure as opposed to a heteroatom substituted ring where a hydrogen on a ring atom is replaced with a heteroatom. For example tetrahydrofuran is a heterocyclic ring and 4-N,N-dimethylamino-phenyl is a heteroatom substituted ring.

As used herein the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

The term "continuous" means a system that operates without interruption or cessation. For example a continuous process to produce a polymer would be one where the reactants are continually introduced into one or more reactors and polymer product is continually withdrawn.

A solution polymerization means a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are preferably not turbid as described in J. Vladimir Oliveira, C. Dariva and J. C. Pinto, Ind. Eng, Chem. Res. 29, 2000, 4627.

A bulk polymerization means a polymerization process in which the monomers and/or comonomers being polymerized are used as a solvent or diluent using little or no inert solvent as a solvent or diluent. A small fraction of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

In a first aspect of the invention there is provided a pyridyl-diamido transition metal complex (optionally for use in alkene polymerization) having the general formula: (I)

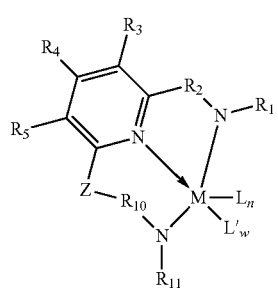

M is a Group 3, 4, 5, 6, 7, 8, 9, 10, 11 or 12 metal (preferably a group 4 metal, preferably Ti, Zr or Hf);
Z is

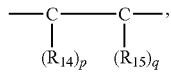

where $R_{14}$ and $R_{15}$ are independently selected from the group consisting of hydrogen, hydrocarbyls, and substituted hydrocarbyls, (preferably hydrogen and alkyls), and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings,
p is 1 or 2, and
q is 1 or 2;
$R_1$ and $R_{11}$ are independently selected from the group consisting of hydrocarbyls, substituted hydrocarbyls, and silyl groups (preferably alkyl, aryl, heteroaryl, and silyl groups);
$R_2$ and $R_{10}$ are each, independently, $-E(R_{12})(R_{13})-$ with E being carbon, silicon, or germanium, and each $R_{12}$ and $R_{13}$ being independently selected from the group consisting of hydrogen, hydrocarbyl, and substituted hydrocarbyl, alkoxy, silyl, amino, aryloxy, halogen, and phosphino (preferably hydrogen, alkyl, aryl, alkoxy, silyl, amino, aryloxy, heteroaryl, halogen, and phosphino), $R_{12}$ and $R_{13}$ may be joined to form a saturated, substituted or unsubstituted hydrocarbyl ring, where the ring has 4, 5, 6, or 7 ring carbon atoms and where substitutions on the ring can join to form additional rings, or $R_{12}$ and $R_{13}$ may be joined to form a saturated heterocyclic ring, or a saturated substituted heterocyclic ring where substitutions on the ring can join to form additional rings;
$R_3$, $R_4$, and $R_5$ are independently selected from the group consisting of hydrogen, hydrocarbyls, substituted hydrocarbyls, alkoxy, aryloxy, halogen, amino, and silyl, (preferably hydrogen, alkyl, alkoxy, aryloxy, halogen, amino, silyl, and aryl), and wherein adjacent R groups ($R_3$ & $R_4$, and/or $R_4$ & $R_5$) may be joined to form a substituted or unsubstituted hydrocarbyl or heterocyclic ring, where the ring has 5, 6, 7, or 8 ring atoms and where substitutions on the ring can join to form additional rings;
L is an anionic leaving group, where the L groups may be the same or different and any two L groups may be linked to form a dianionic leaving group;
n is 0, 1, 2, 3, or 4;
L' is neutral Lewis base; and
w is 0, 1, 2, 3 or 4.

Preferably the R groups above and other R groups mentioned hereafter, contain up to 30, preferably no more than 30 carbon atoms, especially from 2 to 20 carbon atoms.

Preferably M is Ti, Zr, or Hf and/or Z is an aryl group bridging $NR_{11}$, to the remainder of the complex by adjacent carbons of a phenyl ring, and E is carbon, with Zr or Hf based complexes being especially preferred. Z may be an aryl group in which case the two adjacent carbon atoms —C—C— are part of an aryl ring.

In a preferred embodiment, the complexes of this invention are of the general formula IV

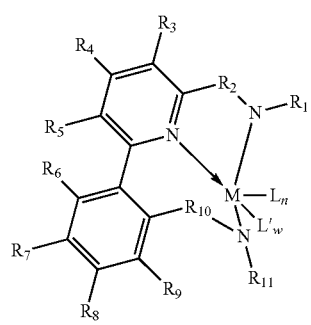

wherein: $R_6$, $R_7$, $R_8$, and $R_9$ are independently selected from the group consisting of hydrogen, hydrocarbyls, substituted hydrocarbyls, alkoxy, halogen, amino, and silyl, and the pairs of positions, and wherein adjacent R groups ($R_6$&$R_7$, and/or $R_7$&$R_5$, and/or $R_5$&$R_5$) may be joined to form a saturated, substituted or unsubstituted hydrocarbyl or heterocyclic ring, where the ring has 5, 6, 7, or 8 ring carbon atoms and where substitutions on the ring can join to form additional rings; and M, L, L', w, n, $R_1$, $R_2$, $R_3$, $R_4$, $R_5$, $R_{10}$ and $R_{11}$ are as defined above.

In a preferred embodiment, $R_1$ and $R_{11}$ may be independently selected from phenyl groups that are variously substituted with between zero to five substituents that include F, Cl, Br, I, $CF_3$, $NO_2$, alkoxy, dialkylamino, aryl, and alkyl groups with between one to ten carbons.

In a preferred embodiment, L may be selected from halide, alkyl, aryl, alkoxy, amido, hydrido, phenoxy, hydroxy, silyl, allyl, alkenyl, and alkynyl. The selection of the leaving groups depends on the synthesis route adopted for arriving at the complex and may be changed by additional reactions to suit the later activation method in polymerization. For example alkyl is preferred when using non-coordinating anions such as N,N-dimethylanilinium tetrakis(pentafluorophenyl)borate or tris(pentafluorophenyl)borane. In another embodiment two L groups may be linked to form a dianionic leaving group, for example oxalate.

In another embodiment, each L' is independently selected from the group consisting of ethers, thio-ethers, amines, nitriles, imines, pyridines, and phosphines, preferably ethers.

The complexes described herein may be arrived through different synthesis routes, all yielding the complex with a tridentate coordinated pyridyldiamido ligand. Exemplary Pyridyldiamido transition metal complex structures are shown below in Chart 1.

Chart 1.

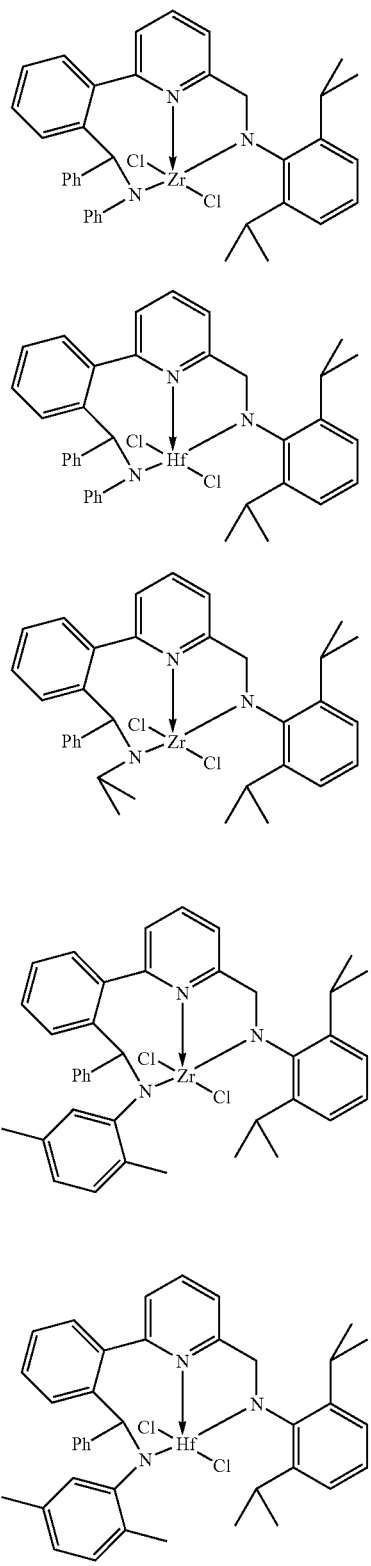

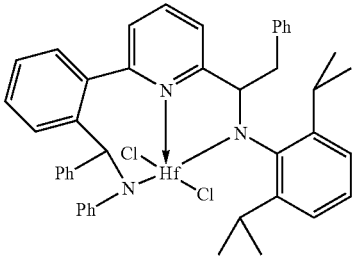

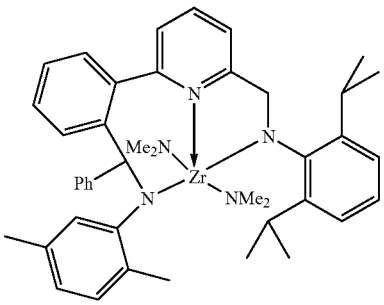

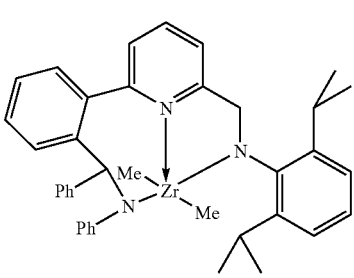

In a second aspect of the invention there are provided various processes for synthesizing the complexes of the first aspect, such as those shown above. Some of these processes may use intermediates that are novel in their own right and form an additional aspect of the invention.

A first synthetic approach relies on the formal insertion of an imine into the metal-carbon bond of an ortho-metallated aryl group of a separately synthesized intermediate pyridylamido metal complex. The insertion of the imine results in the replacement of the metal-carbon bond with a metal-amido bond. Thus the original metal-ligand complex in which the ligand was coordinated to the metal through two nitrogen and one carbon donors, referred to as NNC ligands and complexes, has been fundamentally transformed so that it now coordinates through three nitrogen donors, referred to as NNN ligands and complexes. A compound containing a carbon-nitrogen double bond, such as the imine $R_{11}N{=}C(R_{12})(R_{13})$, may be inserted into a metal-aryl bond to form a NNN complex with one five-membered and one seven-membered chelate ring. $R_{11}$, $R_{12}$ and $R_{13}$ are as defined above. The intermediate pyridylamido metal (NNC) complexes may themselves have catalytic polymerization activity. The invention permits the performance of such intermediate complexes to be modified to arrive at new possibilities in terms of catalyst structures and polymerization performance.

For example the NNN complex C5 shown in Chart 1 above may be made starting from the Hf-containing NNC intermediate complex referred to as Int-5 in the manner described in the examples as the "Synthesis of Int-5 with tridentate N—N—C ligand". Int-5 is analogous to some complexes disclosed in U.S. Pat. No. 6,900,321.

Other, more general, synthetic routes for the preparation of complexes of the type shown in Chart 1 employing pyridyl diamines or their alkali or alkali earth metal derivatives instead of NNC intermediate complexes may be used. The invention may use imines, carbodiimides, isocyanates, isothiocyanates, or other reactants containing carbon-nitrogen double bonds to yield tridentate NNN ligands. Of particular interest in the use of imines, which will give tridentate pyridyldiamido donor ligands. Equation V below shows a general example of the formation of a NNN complex from a NNC complex and a reactant with a carbon-nitrogen double bond

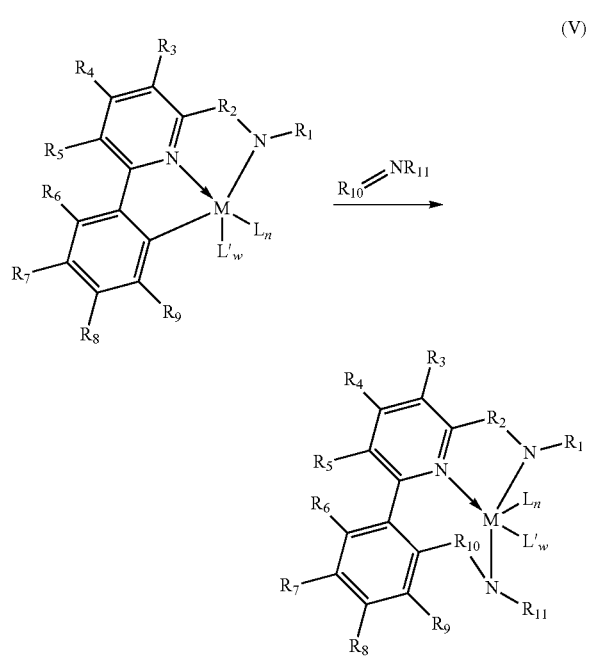

where M, L, L', w, n, $R_1$, $R_2$, $R_3$, $R_4$, $R_5$, $R_6$, $R_7$, $R_8$, $R_9$, $R_{10}$ and $R_{11}$ are as defined above.

A second synthetic approach is to synthesize a suitable novel neutral NNN ancillary ligand precursor that can be then be coordinated with the transition metal in the complex in a tridentate NNN manner. This route differs from the first synthetic approach in that it does not use the NNC complexes as intermediates. One option for this approach is to react a neutral pyridyldiamine with suitable metallo-amide or metallo-organic reagents. For an alternative option to this approach the pyridyldiamine can be deprotonated using an organo-lithium or organo-magnesium reagent and then this pyridyldiamido species can be reacted with a metal halide. One example of the first option is found in the Examples section under the heading "Synthesis of C7 with tridentate N—N—N ligand". That specific example describes the reaction of the pyridyldiamine L4 with the metalloamide $Zr(NMe_2)_4$ to form the NNN complex C7.

The preparation of neutral NNN ligands to use in the second synthetic approach can be done various ways using established synthetic organic chemistry methods and some novel intermediates. One general synthetic route that may be used to prepare pyridyldiamines ligand precursors that have identical substitution (i.e. the R groups are identical in compound E of Scheme 1) of the amines is shown in the top part of Scheme 1. In the first step the commercially available (Sigma-Aldrich) boronic acid A is coupled with B using Suzuki-type conditions to yield the dialdehyde C. Typical reaction conditions would use one equivalent of boronic acid A, 0.8 to 1.2 equivalents of compound B, 1.0 to 1.4 equivalents of $Na_2CO_3$, 0.001 to 0.05 equivalents of a suitable catalysts such as $Pd(PPh_3)_4$, and a biphasic mixture of solvents comprised of approximately equal volumes of toluene and 4:1 water:methanol.

The di-aldehyde is a novel compound that may be used as an intermediate in other syntheses. Thus invention also provides novel compounds for making the ligand precursors. The dialdehyde has the general formula:

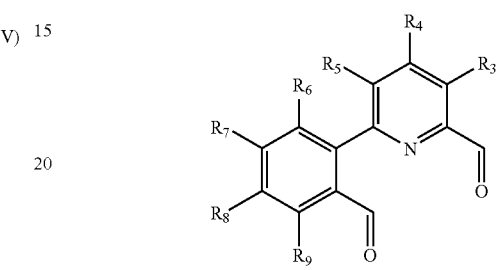

where $R_3$ to $R_9$ are as defined above.

The dialdehyde C can react with an aryl or alkyl amine in the presence of an acid catalyst to form the di-imine D as shown in Scheme 1. Compound D can then be reduced with various hydride sources to form the pyridyldiamine E. Typical reaction conditions that can be used are as follows. One molar equivalent of the dialdehyde C is combined with 2.0 equivalents of the amine, 0.00 to 0.05 equivalents of an acid catalyst such as p-toluenesulfonic acid monohydrate (Sigma-Aldrich), and toluene or benzene solvent to form a mixture that is between 0.05 and 1.0 M in the starting dialdehyde. The mixture is heated to reflux while fitted with a Dean-Stark trap to remove the water formed via azeotropic distillation. After 2 to 48 hours removal of the volatiles affords the diimine D. The diimine D can be reduced to the diamine E by reaction of 0.1 to 1.0 M solutions of D in etherial solvents, such as diethyl ether or tetrahydrofuran, with 0.3 to 1.4 molar equivalents of $LiAlH_4$. Alternatively $NaBH_4$ in alcohol or other borohydride reductants may be used in place of $LiAlH_4$.

A second general synthetic route to neutral NNN ligands is demonstrated in the bottom part of Scheme 1. This general synthetic route is especially versatile in that it can be used to make unsymmetrically substituted pyridyl diamines such as compound M in Scheme 1 where R is not equal to R". The sequence may begin with the formation of imine F by reaction of the aldehyde B with an alkyl or aryl amine. Typically one molar equivalent of the aldehyde B is mixed with one equivalent of the amine in toluene or benzene to form a solution that is between 0.05 and 1.0 M in the aldehyde B. Then 0.001 to 0.05 molar equivalents of an acid catalyst such as p-toluenesulfonic acid monohydrate is added and the mixture is heated to reflux while fitted with a Dean-Stark trap to remove water that is formed. The product F can then be reacted with either organo-lithium or Grignard to form the amine G. Alternatively, compound F could be reduced with a hydride source, such as $LiAlH_4$, to form G'. Compound G can then be coupled with the boronic acid A using Suzuki reaction conditions identical to those described above to form compound K.

The intermediate used for preparing asymmetrically substituted ligand precursors may use a compound that permits successive aminations. Accordingly the invention also provides a novel compound Ix as follows:

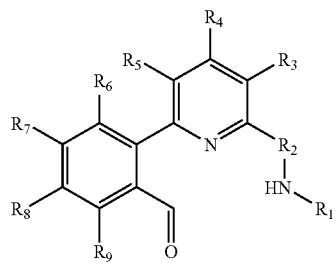

(IX)

wherein $R_1$, $R_2$, and $R_3$ to $R_9$ are as defined above.

The aldehyde K can then be reacted with primary amines to form the imine J. The reaction conditions are the same as those described above for the formation of compound F. Compound J can be reduced to the diamine L by reaction of 0.1 to 1.0 M solutions of D in etherial solvents, such as diethyl ether or tetrahydrofuran, with 0.3 to 1.4 molar equivalents of LiAlH$_4$. Alternatively NaBH$_4$ in alcohol or other borohydride reductants may be used in place of LiAlH$_4$.

The reaction schemes discussed above for making the ancillary ligand precursors are set out below:

Scheme 1. A couple of synthetic routes to pyridyldiamine ligands.

route for symmetrically substituted amine groups

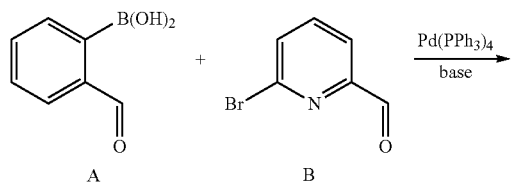

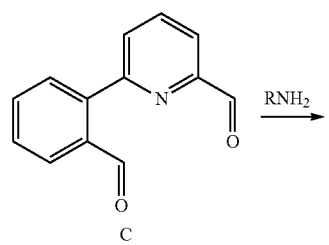

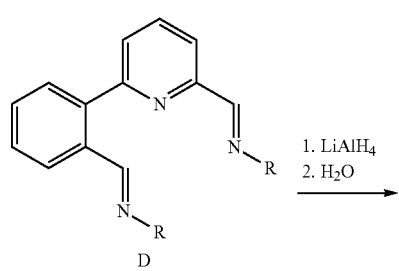

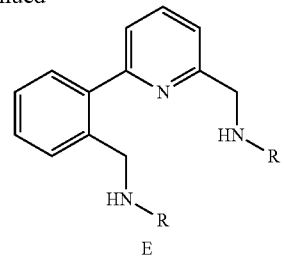

route for unsymmetrically substituted amine groups

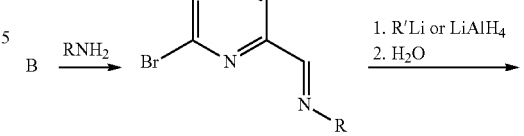

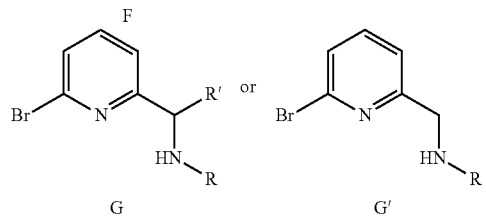

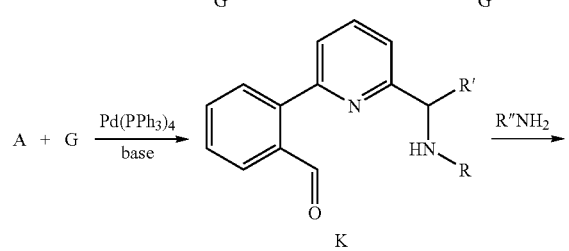

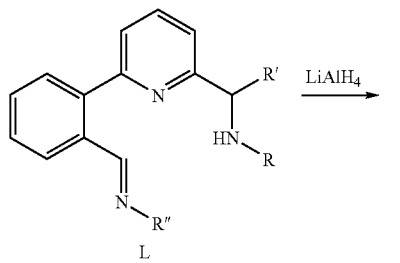

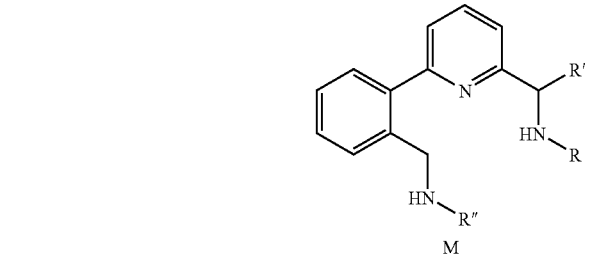

where R, R', R" are, independently, hydrocarbyl or substituted hydrocarbyl, preferably alkyl groups.

These synthetic process options may result in the ancillary ligand precursors below that may be used also to make the complexes shown in Chart 1 above by reaction with an appropriate organometallic or metalloamide reagent or by reaction of the pyridyldiamido derivatives, via deprotonation with organolithium or organomagnesium reagents, and with a transition metal salt.

Chart 2. Pyridyldiamine ligands and their abbreviations

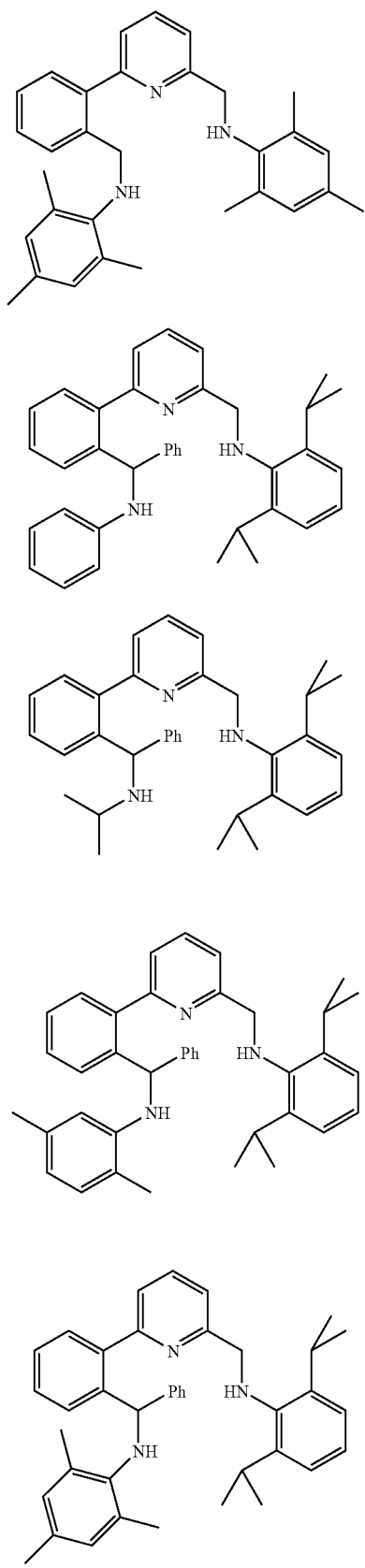

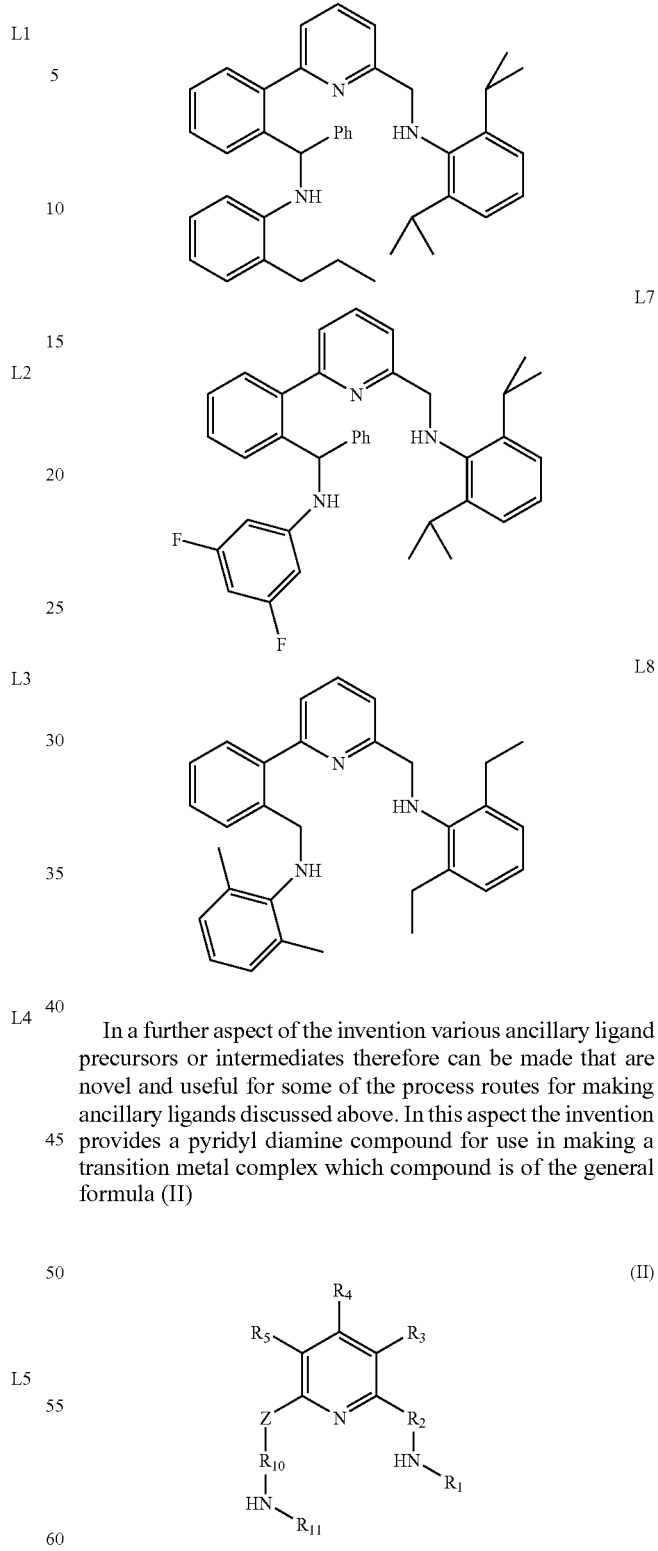

In a further aspect of the invention various ancillary ligand precursors or intermediates therefore can be made that are novel and useful for some of the process routes for making ancillary ligands discussed above. In this aspect the invention provides a pyridyl diamine compound for use in making a transition metal complex which compound is of the general formula (II)

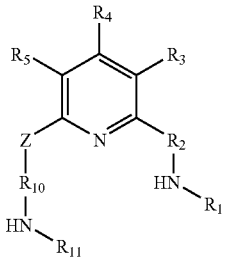

wherein Z, $R_1$ to $R_5$, $R_{10}$ and $R_{11}$ have the meaning indicated above.

As for the transition metal complexes themselves the substitution patterns may be varied widely to provide an extensive range of structural option for the final transition metal complex. For preferred complexes, the ancillary ligand precursors may have a structure where Z may be an aryl group as shown in the general formula (III)

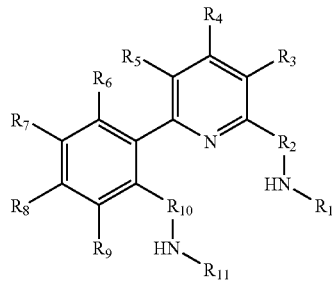

with $R_1$ to $R_{11}$ being independently selected as indicated above.

The synthesized complexes may be used as the transition metal components for catalysts used for polymerizing or oligomerizing alkenes. These complexes may be used in combination with appropriate activators for olefin polymerization such as ethylene-based polymers or propylene-based polymers, including ethylene-octene polymerization. They may also have activity in ethylene oligomerization and may be highly active.

In further embodiments, it is preferred that $R_1$ to $R_{13}$ contain up to 30 and no more than 30 carbon atoms, especially from 2 to 20 carbon atoms. $R_1$ and $R_{11}$ substituted on the nitrogen atom are preferably selected from aryl group containing from 6 to 30 carbon atoms, especially phenyl groups. It is preferred that $R_1$ and $R_{11}$ be chosen from aryl or alkyl groups and that $R_{12}$ through $R_{15}$ be independently chosen from hydrogen, alkyl, and aryl groups, such as phenyl. The phenyl groups may be alkyl substituted. The alkyl substituents may be straight chain alkyls but include branched alkyls.

Preferably each $R_1$ and $R_{11}$ are a substituted phenyl group with either one or both of the carbons adjacent to the carbon joined to the amido nitrogen being substituted with an group containing between one to ten carbons. Some specific examples would include $R_1$ and $R_{11}$ being chosen from a group including 2-methylphenyl, 2-isopropylphenyl, 2-ethylphenyl, 2,6-dimethylphenyl, mesityl, 2,6-diethylphenyl, and 2,6-diisopropylphenyl.

$R_2$ is preferably selected from moieties where E is carbon, especially a moiety —C($R_{12}$)($R_{13}$)— where $R_{12}$ is hydrogen and $R_{13}$ is an aryl group or a benzyl group (preferably a phenyl ring linked through an alkylene moiety such as methylene to the C atom). The phenyl group may then be substituted as discussed above. Preferably $R_3$ to $R_9$ are hydrogen or alkyl from 1 to 4 carbon atoms. Preferably 0, 1 or 2 of $R_3$ to $R_9$ are alkyl substituents.

The pyridyldiamido-metal complex I is coordinated the metal center as a tridentate ligand through two amido donors and one pyridyl donor. The metal center M is a transition metal from Groups 3 to 12. While in its use as a catalyst, according to current theory M is preferably in its four valent state, it is possible to create compounds in which M has a reduced valency state and regains its formal valency state upon preparation of the catalysts system by contacting with an activator. Preferably in addition to the pyridyldiamido ligand, the metal M is also coordinated to n number of anionic ligands, with n being from 1 to 4. The anionic donors are typically halide or alkyl, but a wide range of other anionic groups are possible including some that are covalently linked together to form molecules that could be considered dianionic, such as oxalate. For certain complexes it is likely that up to three neutral Lewis bases (L'), typically ethers, could also be coordinated to the metal center. In a preferred embodiment w is 0, 1, 2 or 3.

For stereoregular forms of polymerization, and/or variations in the polymerization properties within isomeric structures, preferably Z is an aryl group and $R_{12}$ is not the same as $R_{13}$ and $R_{14}$ is not the same as $R_{15}$. Preferably $R_2$ and $R_{10}$ are centers of chirality. Suitably then the seven-membered chelate ring formed by M—N—$R_{10}$—C—C—C—N introduces a third chiral element due to the conformation adopted by the large ring, as shown in the solid-state structures in FIGS. 1 and 2. This is also indicated in the $^1$H-NMR data for many of the NNN complexes, such as C1, presented in the experimental section. Thus diastereoisomeric mixtures of complexes are accessible, which when used with activators to oligomerize or polymerize alkenes may give polyolefin products with broad polydispersities relative to typical "single-site" catalysts which demonstrate $M_n/M_w$ values typically around 2. E is preferred to be carbon.

Many of the options and synthesis steps are described in connection with the preparation of complexes having analogous tridentate NNC ligand systems as referred to above. These details will focus on the options within the broad categories described previously and the differences from previous synthesis options having tridentate NNC configurations.

In one preferred embodiment Z is defined as an aryl so that the complex corresponds to formula IV, and E is defined as carbon, and M is defined as Zr and/or Hf, and $R_1$ and $R_{11}$ are aryl groups each containing between 6 to 20 carbons.

A preferred synthesis of the pyridyldiamido complexes is reaction of the neutral pyridyldiamine ligand precursors with a metalloamide, including $Zr(NMe_2)_4$, $Zr(NEt_2)_4$, $Hf(NMe_2)_4$, and $Hf(NEt_2)_4$. Another preferred synthesis of the pyridyldiamido complexes is the reaction of the neutral pyridyldiamine ligand precursors with an organolithium reagent to form the dilithio pyridyldiamido derivative followed by reaction of this species with either a transition metal salt, including $ZrCl_4$, $HfCl_4$, $ZrCl_4$(1,2-dimethoxyethane), $HfCl_4$(1,2-dimethoxyethane), $ZrCl_4$(tetrahydrofuran)$_2$, $HfCl_4$(tetrahydrofuran)$_2$, $ZrBn_2Cl_2$(OEt$_2$), $HfBn_2Cl_2$(OEt$_2$). Another preferred synthesis of the pyridyldiamido complexes is reaction of the neutral pyridyldiamine ligand precursors with an organometallic reactant, including $ZrBn_4$, $ZrBn_2Cl_2$(OEt$_2$), $Zr(CH_2SiMe_3)_4$, $Zr(CH_2CMe_3)_4$, $HfBn_4$, $HfBn_2Cl_2$(OEt$_2$), $Hf(CH_2SiMe_3)_4$, $Hf(CH_2CMe_3)_4$.

In another embodiment, Z is a 5 membered ring (such as substituted or unsubstituted cyclopentadiene, "Cp"). In a particular embodiment, Z is a ferrocenyl group where one of the Cp rings links to $R_{10}$ to the pyridyl ring.

Activators

After the complexes have been synthesized, catalyst systems may be formed by combining them with activators in any manner known from the literature including by supporting them for use in slurry or gas phase polymerization. The catalyst systems may also be added to or generated in solution polymerization or bulk polymerization (in the monomer). The catalyst system typically comprise a complex as described above and an activator such as alumoxane or a non-coordinating anion. Activation may be performed using alumoxane solution including methyl alumoxane, referred to as MAO, as well as modified MAO, referred to herein as MMAO, containing some higher alkyl groups to improve the solubility. Particularly useful MAO can be purchased from Albemarle in a 10 wt % solution in toluene. The catalyst system employed in the present invention preferably uses an activator selected from alumoxanes, such as methyl alumoxane, modified methyl alumoxane, ethyl alumoxane, iso-butyl alumoxane and the like.

When an alumoxane or modified alumoxane is used, the complex-to-activator molar ratio is from about 1:3000 to 10:1; alternatively, 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-complex ratio is 1:1 molar ratio.

Activation may also be performed using non-coordinating anions, referred to as NCA's, of the type described in EP 277 003 A1 and EP 277 004 A1. NCA may be added in the form of an ion pair using, for example, [DMAH]$^+$[NCA]$^-$ in which the N,N-dimethylanilinium (DMAH) cation reacts with a basic leaving group on the transition metal complex to form a transition metal complex cation and [NCA]$^-$. The cation in the precursor may, alternatively, be trityl. Alternatively, the transition metal complex may be reacted with a neutral NCA precursor, such as B($C_6F_5$)$_3$, which abstracts an anionic group from the complex to form an activated species. Useful activators include N,N-dimethylanilinium tetrakis (pentafluorophenyl)borate (i.e., [PhNMe$_2$H]B($C_6F_5$)$_4$) and N,N-dimethylanilinium tetrakis (heptafluoronaphthyl)borate, where Ph is phenyl, and Me is methyl.

Additionally preferred activators useful herein include those described in U.S. Pat. No. 7,247,687 at column 169, line 50 to column 174, line 43, particularly column 172, line 24 to column 173, line 53.

When an NCA (such as an ionic or neutral stoichiometric activator) is used, the complex-to-activator molar ratio is typically from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2.

Alternately a co-activator may also be used in the catalyst system herein. The complex-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Supports

The complexes described herein may be supported (with or without an activator) by any method effective to support other coordination catalyst systems, effective meaning that the catalyst so prepared can be used for oligomerizing or polymerizing olefin in a heterogeneous process. The catalyst precursor, activator, co-activator if needed, suitable solvent, and support may be added in any order or simultaneously. Typically, the complex and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours. But greater or lesser times and temperatures are possible.

The complex may also be supported absent the activator; in that case, the activator (and co-activator if needed) is added to a polymerization process's liquid phase. Additionally, two or more different complexes may be placed on the same support. Likewise, two or more activators or an activator and co-activator may be placed on the same support.

Suitable solid particle supports are typically comprised of polymeric or refractory oxide materials, each being preferably porous. Preferably any support material that has an average particle size greater than 10 μm is suitable for use in this invention. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component, however, an additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Useful supports typically have a surface area of from 10-700 m$^2$/g, a pore volume of 0.1-4.0 cc/g and an average particle size of 10-500 μm. Some embodiments select a surface area of 50-500 m$^2$/g, a pore volume of 0.5-3.5 cc/g, or an average particle size of 20-200 μm. Other embodiments select a surface area of 100-400 m$^2$/g, a pore volume of 0.8-3.0 cc/g, and an average particle size of 30-100 μm. Useful supports typically have a pore size of 10-1000 Angstroms, alternatively 50-500 Angstroms, or 75-350 Angstroms.

The catalyst complexes described herein are generally deposited on the support at a loading level of 10-100 micromoles of complex per gram of solid support; alternately 20-80 micromoles of complex per gram of solid support; or 40-60 micromoles of complex per gram of support. But greater or lesser values may be used provided that the total amount of solid complex does not exceed the support's pore volume.

Polymerization

Invention catalyst complexes are useful in polymerizing unsaturated monomers conventionally known to undergo metallocene-catalyzed polymerization such as solution, slurry, gas-phase, and high-pressure polymerization. Typically one or more of the complexes described herein, one or more activators, and one or more monomers are contacted to produce polymer. The complexes may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The complexes, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the complex is activated in the reactor in the presence of olefin.

In a particularly preferred embodiment, the polymerization process is a continuous process.

Polymerization process used herein typically comprise contacting one or more alkene monomers with the complexes (and, optionally, activator) described herein. For purpose of this invention alkenes are defined to include multi-alkenes (such as dialkenes) and alkenes having just one double bond. Polymerization may be homogeneous (solution or bulk polymerization) or heterogeneous (slurry—in a liquid diluent, or gas phase—in a gaseous diluent). In the case of heterogeneous slurry or gas phase polymerization, the complex and activator may be supported. Silica is useful as a support herein. Chain transfer agents (such as hydrogen, or diethyl zinc) may be used in the practice of this invention.

The present polymerization processes may be conducted under conditions preferably including a temperature of about 30° C. to about 200° C., preferably from 60° C. to 195° C., preferably from 75° C. to 190° C. The process may be conducted at a pressure of from 0.05 to 1500 MPa. In a preferred embodiment, the pressure is between 1.7 MPa and 30 MPa, or in another embodiment, especially under supercritical conditions, the pressure is between 15 MPa and 1500 MPa.

Monomers

Monomers useful herein include olefins having from 2 to 20 carbon atoms, alternately 2 to 12 carbon atoms (preferably ethylene, propylene, butylene, pentene, hexene, heptene, octene, nonene, decene, and dodecene) and optionally also polyenes (such as dienes). Particularly preferred monomers include ethylene, and mixtures of $C_2$ to $C_{10}$ alpha olefins, such as ethylene-propylene, ethylene-hexene, ethylene-octene, propylene-hexene, and the like.

The complexes described herein are also particularly effective for the polymerization of ethylene, either alone or in combination with at least one other olefinically unsaturated monomer, such as a $C_3$ to $C_{20}$ α-olefin, and particularly a $C_3$ to $C_{12}$ α-olefin. Likewise the present complexes are also particularly effective for the polymerization of propylene, either alone or in combination with at least one other olefinically unsaturated monomer, such as ethylene or a $C_4$ to $C_{20}$ α-olefin, and particularly a $C_4$ to $C_{20}$ α-olefin. Examples of preferred α-olefins include ethylene, propylene, butene-1, pentene-1, hexene-1, heptene-1, octene-1, nonene-1, decene-1, dodecene-1,4-methylpentene-1,3-methylpentene-1,3,5,5-trimethylhexene-1, and 5-ethylnonene-1.

In some embodiments the monomer mixture may also comprise one or more dienes at up to 10 wt %, such as from 0.00001 to 1.0 wt %, for example from 0.002 to 0.5 wt %, such as from 0.003 to 0.2 wt %, based upon the monomer mixture. Non-limiting examples of useful dienes include, cyclopentadiene, norbornadiene, dicyclopentadiene, 5-ethylidene-2-norbornene, 5-vinyl-2-norbornene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1 and 9-methyl-1,9-decadiene.

Where olefins are used that give rise to short chain branching, such as propylene, the catalyst systems may, under appropriate conditions, generate stereoregular polymers or polymers having stereoregular sequences in the polymer chains.

Scavengers

In some embodiments, when using the complexes described herein, particularly when they are immobilized on a support, the catalyst system will additionally comprise one or more scavenging compounds. Here, the term scavenging compound means a compound that removes polar impurities from the reaction environment. These impurities adversely affect catalyst activity and stability. Typically, the scavenging compound will be an organometallic compound such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfp)_4]^-$ or $B(pfp)_3$ (perfluorophenyl=pfp=$C_6F_5$).

In a preferred embodiment, two or more complexes are combined with diethyl zinc in the same reactor with monomer. Alternately one or more complexes is combined with another catalyst (such as a metallocene) and diethyl zinc in the same reactor with monomer.

Polymer Products

While the molecular weight of the polymers produced herein is influenced by reactor conditions including temperature, monomer concentration and pressure, the presence of chain terminating agents and the like, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by GPC. Preferred polymers produced here may be homopolymers or copolymers. In a preferred embodiment the comonomer(s) are present at up to 50 mol %, preferably from 0.01 to 40 mol %, preferably 1 to 30 mol %, preferably from 5 to 20 mol %.

End Uses

Articles made using polymers produced herein may include, for example, molded articles (such as containers and bottles, e.g. household containers, industrial chemical containers, personal care bottles, medical containers, fuel tanks, and storageware, toys, sheets, pipes, tubing) films, non-wovens, and the like. It should be appreciated that the list of applications above is merely exemplary, and is not intended to be limiting.

In another embodiment, this invention relates to:
1. A pyridyldiamido transition metal complex for use in alkene polymerization having the general formula (I)

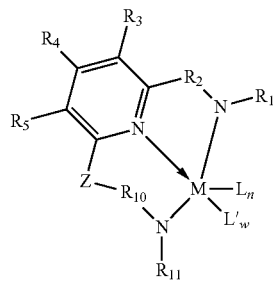

(I)

wherein:
M is a Group 3, 4, 5, 6, 7, 8, 9, 10, 11 or 12 metal;
Z is

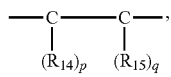

where $R_{14}$ and $R_{15}$ are independently selected from the group consisting of hydrogen, hydrocarbyls (such as alkyls), and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings,
p is 0, 1 or 2, and
q is 0, 1 or 2;
$R_1$ and $R_{11}$ are independently selected from the group consisting of hydrocarbyls (such as alkyls and aryls), substituted hydrocarbyls (such as heteroaryls), and silyl groups;
$R_2$ and $R_{10}$ are each, independently, $-E(R_{12})(R_{13})-$ with E being carbon, silicon, or germanium, and each $R_{12}$ and $R_{13}$ being independently selected from the group consisting of hydrogen, hydrocarbyls (such as alkyls, aryls), alkoxy, silyl, amino, aryloxy, substituted hydrocarbyls (such as heteroaryl), halogen, and phosphino, $R_{12}$ and $R_{13}$ may be joined to form a saturated, substituted or unsubstituted hydrocarbyl ring, where the ring has 4, 5, 6, or 7 ring carbon atoms and where substitutions on the ring can join to form additional rings, or $R_{12}$ and $R_{13}$ may be joined to form a saturated heterocyclic ring, or a saturated substituted heterocyclic ring where substitutions on the ring can join to form additional rings;
$R_3$, $R_4$, and $R_5$ are independently selected from the group consisting of hydrogen, hydrocarbyls (such as alkyls and aryls), substituted hydrocarbyls, alkoxy, aryloxy, halogen, amino, and silyl, and wherein adjacent R groups ($R_3$ & $R_4$, and/or $R_4$ & $R_5$) may be joined to form a substituted or unsubstituted hydrocarbyl or heterocyclic ring, where the ring has 5, 6, 7, or 8 ring atoms and where substitutions on the ring can join to form additional rings;
L is an anionic leaving group, where the L groups may be the same or different and any two L groups may be linked to form a dianionic leaving group;
n is 0, 1, 2, 3, or 4;
L' is neutral Lewis base; and
w is 0, 1, 2, 3 or 4.

2. Complex according to paragraph 1 in which M is Ti, Zr, or Hf and/or Z is a substituted aryl group bridging $NR_{11}$, to the remainder of the complex by a chain of three adjacent atoms of which two are adjacent carbons of a substituted phenyl ring and the third is covalently bonded to one of these two carbons.

3. Complex according to paragraph 1 or paragraph 2 in which Z is an aryl group so that the complex is of the general formula IV

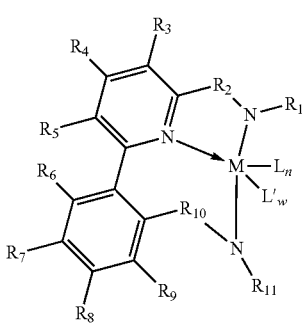

(IV)

wherein
$R_6$, $R_7$, $R_8$, and $R_9$ are independently selected from the group consisting of hydrogen, hydrocarbyls (such as alkyls and aryls), substituted hydrocarbyls, alkoxy, halogen, amino, and silyl, and the pairs of positions, and wherein adjacent R groups ($R_6$&$R_7$, and/or $R_7$&$R_8$, and/or $R_8$&$R_9$) may be joined to form a saturated, substituted or unsubstituted hydrocarbyl or heterocyclic ring, where the ring has 5, 6, 7, or 8 ring carbon atoms and where substitutions on the ring can join to form additional rings; and M, L, L', w, n, $R_1$, $R_2$, $R_3$, $R_4$, $R_5$, $R_{10}$ and
$R_{11}$ are as defined in paragraph 1.

4. Complex according to any of the preceding paragraphs 1 to 3 in which $R_1$ and $R_3$ to $R_9$ and/or $R_{11}$ to $R_{15}$ above contain no more than 30 carbon atoms, especially from 2 to 20 carbon atoms.

5. Complex according to any of the preceding paragraphs 1 to 4 in which E is carbon and $R_1$ and $R_{11}$ are independently selected from phenyl groups that are variously substituted with between zero to five substituents that include F, Cl, Br, I, $CF_3$, $NO_2$, alkoxy, dialkylamino, hydrocarbyl (such as alkyl and aryl), and substituted hydrocarbyls (such as heteroaryl), groups with from one to ten carbons.

6. Complex according to any of the preceding paragraphs 1 to 5 in which L is or are selected from halide, alkyl, aryl, alkoxy, amido, hydrido, phenoxy, hydroxy, silyl, allyl, alkenyl, and alkynyl; and L' is or are selected from ethers, thio-ethers, amines, nitriles, imines, pyridines, and phosphines.

7. Process for preparing a pyridyldiamido complex according to any of the preceding paragraphs 1 to 6 comprising the formal insertion of an imine into the metal-carbon bond of an ortho-metalated aryl group of a separately synthesized intermediate pyridylamido metal complex as shown in equation V

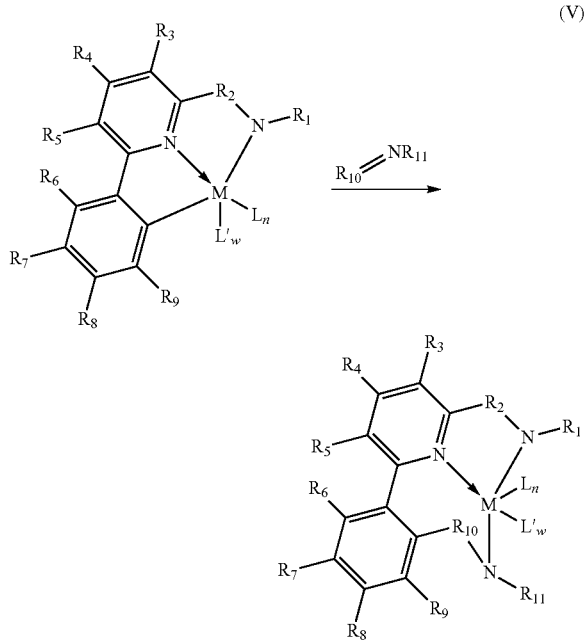

(V)

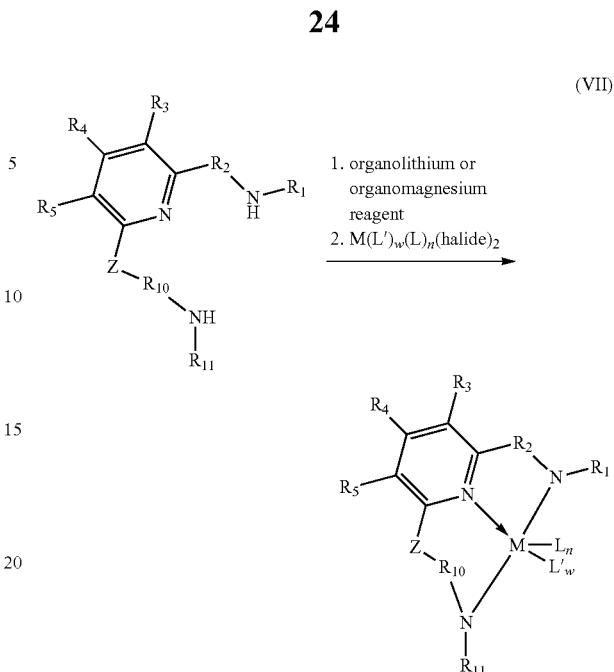

(VII)

wherein M, L, L', w, n, $R_1$, $R_2$, $R_3$, $R_4$, $R_5$, $R_6$, $R_7$, $R_8$, $R_9$, $R_{10}$ and $R_{11}$ are as defined in paragraph 1 and 3.

8. Process for preparing a complex according to any of the preceding paragraphs 1 to 6 comprising reaction of a pyridyldiamine with metallo-amide or metallo-organic reagents as shown in equation VI

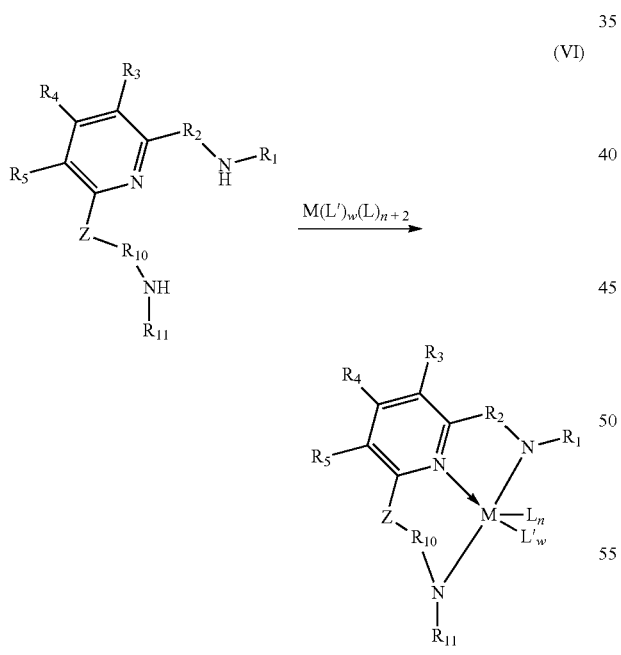

(VI)

wherein M, L, L', Z, w, n, $R_1$, $R_2$, $R_3$, $R_4$, $R_5$, $R_{10}$ and $R_{11}$ are as defined in paragraph 1.

9. Process for preparing a complex according to any of the preceding paragraphs 1 to 6 in which a pyridyldiamine is deprotonated using an organolithium or organomagnesium reagent and then this pyridyldiamido reagent is reacted with a metal halide as shown in equation VII.

wherein M, L, L', Z, w, n, $R_1$, $R_2$, $R_3$, $R_4$, $R_5$, $R_{10}$ and $R_{11}$ are as defined in paragraph 1.

10. A pyridyldiamine compound for use in making a transition metal complex which compound is of the general formula (II)

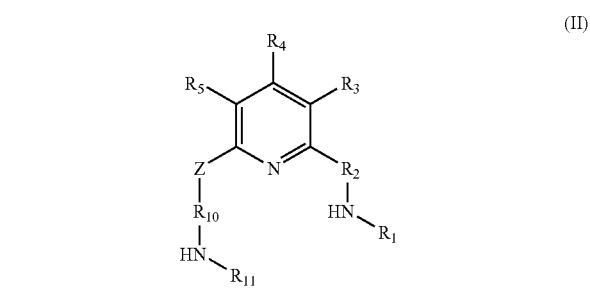

(II)

wherein Z is,

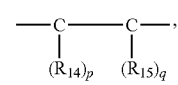

where $R_{14}$ and $R_{15}$ are independently selected from the group consisting of hydrogen hydrocarbyls (such as alkyls) and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings, p is 0, 1 or 2, and q is 0, 1 or 2;

$R_1$ and $R_{11}$ are independently selected from the group consisting of alkyl, aryl, heteroaryl, or silyl groups;

$R_2$ and $R_{10}$ are each, independently, -E($R_{12}$)($R_{13}$)— with E being carbon, silicon, or germanium, and each $R_{12}$ and $R_{13}$ being independently selected from the group consisting of hydrogen, hydrocarbyls (such as alkyls and aryls), substituted hydrocarbyls (such as heteroaryl), alkoxy, silyl, amino, aryloxy, halogen, and phosphino, $R_{12}$ and $R_{13}$ may be joined to form a saturated, substituted or unsubstituted hydrocarbyl ring, where the ring has 4, 5, 6, or 7 ring carbon atoms and where substitutions on the ring can join to form additional rings, or $R_{12}$ and $R_{13}$ may be joined to form a saturated heterocyclic ring, or a saturated substituted heterocyclic ring where substitutions on the ring can join to form additional rings; and $R_3$, $R_4$, and $R_5$ are independently selected from the group consisting of hydrogen, hydrocarbyls (such as alkyls), substituted hydrocarbyls, alkoxy, aryloxy, halogen, amino, and silyl, and wherein adjacent R groups ($R_3$ & $R_4$, and/or $R_4$ & $R_5$) may be joined to form a substituted or unsubstituted hydrocarbyl or heterocyclic ring, where the ring has 5, 6, 7, or 8 ring atoms and where substitutions on the ring can join to form additional rings.

11. Compound according to paragraph 10 in which Z is an aryl group as shown in the general formula (III)

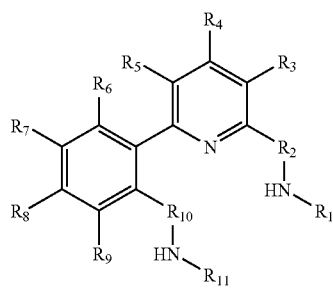

(III)

wherein: $R_6$, $R_7$, $R_8$, and $R_9$ are independently selected from the group consisting of hydrogen, hydrocarbyls (such as alkyls), substituted hydrocarbyls, alkoxy, halogen, amino, and silyl, and the pairs of positions, and wherein adjacent R groups ($R_6$&$R_7$, and/or $R_7$&$R_8$, and/or $R_8$&$R_9$) may be joined to form a saturated, substituted or unsubstituted hydrocarbyl or heterocyclic ring, where the ring has 5, 6, 7, or 8 ring carbon atoms and where substitutions on the ring can join to form additional rings; and
wherein $R_1$, $R_2$, $R_3$, $R_4$, $R_5$, $R_{10}$ and $R_{11}$ are as defined in paragraph 1.

12. A pyridyl-derivative of the general formula VIII

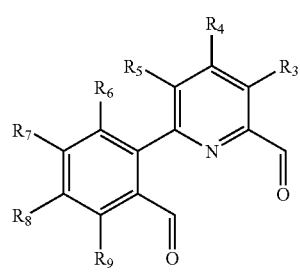

(VIII)

wherein $R_3$, $R_4$, $R_5$, $R_6$, $R_7$, $R_5$, and $R_9$ are independently selected from the group consisting of hydrogen, hydrocarbyls (such as alkyls, substituted hydrocarbyls alkoxy, aryloxy, halogen, amino, and silyl, and wherein adjacent R groups ($R_3$ & $R_4$, and/or $R_4$ & $R_5$, and/or $R_6$ & $R_7$, and/or $R_7$ & $R_8$, and/or $R_8$&$R_9$) may be joined to form a substituted or unsub- stituted hydrocarbyl or heterocyclic ring, where the ring has 5, 6, 7, or 8 ring atoms and where substitutions on the ring can join to form additional rings.

13. A pyridyl derivative of the general formula (IX)

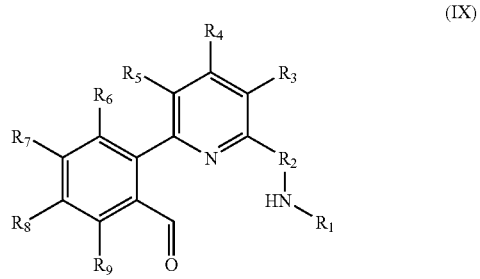

(IX)

wherein $R_1$ is independently selected from the group consisting of hydrocarbyls (such as alkyls and aryls), substituted hydrocarbyls (heteroaryls), and silyl groups, $R_2$ is -E($R_{12}$)($R_{13}$)— with E being carbon, silicon, or germanium, each $R_{12}$ and $R_{13}$ being independently selected from the group consisting of hydrogen, hydrocarbyls (such as alkyls and aryls), substituted hydrocarbyls, alkoxy, silyl, amino, halogen, and phosphino, $R_3$, $R_4$, $R_5$, $R_6$, $R_7$, $R_8$, and $R_9$ are independently selected from the group consisting of hydrogen, hydrocarbyls (such as alkyls and aryls), substituted hydrocarbyls, alkoxy, aryloxy, halogen, amino, and silyl, and wherein adjacent R groups ($R_3$ & $R_4$, and/or $R_4$ & $R_5$, and/or $R_6$ & $R_7$, and/or $R_7$ & $R_8$, and/or $R_8$&$R_9$) may be joined to form a substituted or unsubstituted hydrocarbyl or heterocyclic ring, where the ring has 5, 6, 7, or 8 ring atoms and where substitutions on the ring can join to form additional rings.

14. Catalyst system comprising a complex according to any of paragraphs 1 to 6 and an activator or cocatalyst such as alumoxane or a non-coordinating anion.

15. Polymerization process comprising contacting alkene monomer with a catalyst according to claim 14 to make a polyalkene.

EXAMPLES

Examples of Synthesis of Ligand Precursors

Synthesis of N—N bidentate Ligand Precursor Int-1 (not according to Invention)

Int-1 (structure below) is an intermediate used for synthesizing complexes with tridentate N—N—C ligands. 2-Phenyl-6-pyridinecarboxaldehyde (4.08 g, 22.3 mmol) and 2,6-diisopropylaniline (3.95 g, 22.3 mmol) were mixed with benzene (125 mL). Then p-toluenesulfonic acid monohydrate (0.010 g, 0.05 mmol) was added (cat. acid in reaction scheme below). The mixture was heated to reflux for 4 hours while fitted with a Dean-Stark trap. The removal of the volatiles under reduced pressure at 40-50° C. afforded the pyridyl imine Int-1 as a yellow crystalline solid. Yield: 7.35 g, 96.2%.
$^1$H NMR (250 MHz, $C_6D_6$): δ 8.69 (1H, s), 8.34 (1H, d), 8.14 (2H, d), 7.2-7.4 (8H, m), 3.27 (2H, sept), 1.25 (12H, d). The general reaction scheme is illustrated below:

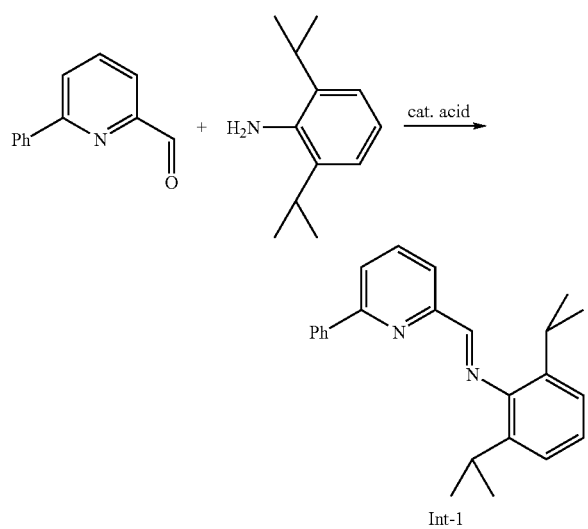

Int-1

Synthesis of N—N Bidentate Ligand Precursor Int-2 (not According to Invention)

Int-2 (structure below) is an intermediate used for synthesizing complexes with tridentate N—N—C ligands. Tetrahydrofuran (10 mL) was added to 2,6-diisopropylaniline (0.454 g, 2.56 mmol) and 3 angstrom molecular sieves (ca. 15 mL). Then solid 2-phenyl-6-pyridinecarboxaldehyde (0.469 g, 2.56 mmol) and p-toluenesulfonic acid monohydrate (0.004 g, 0.02 mmol) were added (cat. acid in reaction scheme below). The mixture was heated to 65° C. in a sealed flask. After heating overnight the mixture was cooled and solid LiAlH$_4$ (0.243 g, 6.40 mmol) was added in small portions over 10 minutes. The mixture was stirred for 20 minutes and then water was carefully added. The organics were extracted into Et$_2$O (30 mL) and dried over MgSO$_4$. Evaporation of the volatiles afforded the pyridyl amine Int-2 as a very pale yellow oil. Yield: 0.86 g, 98%. $^1$H NMR (250 MHz, C$_6$D$_6$): δ 8.11 (2H, d), 7.32-7.04 (8H, m), 6.74 (1H, d), 4.75 (1H, br), 4.28 (2H, s), 3.66 (2H, sept), 1.26 (12H, d). The general reaction scheme is illustrated below.

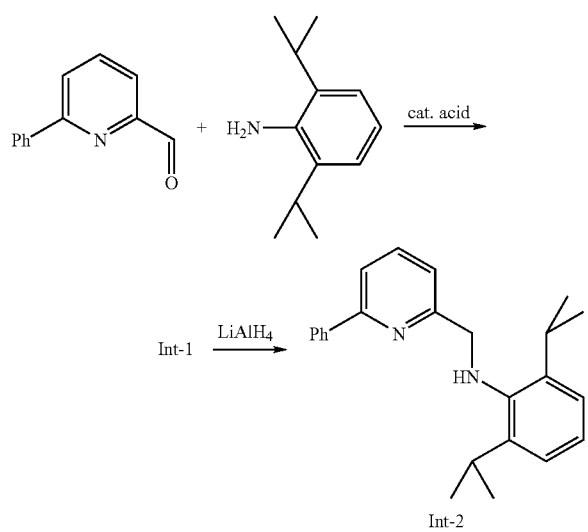

Int-2

Examples

Synthesis of Transition Metal Complexes

Synthesis of Int-3 with Tridentate N—N—C Ligand (not According to Invention)

Int-3 (structure below) is used as intermediate for making N—N—N complexes. A benzene (5 mL) solution of ZrBn$_2$Cl$_2$(OEt$_2$) (0.532 g, 1.27 mmol) was added dropwise over 30 seconds to a benzene (5 mL) solution of Int-2 (0.438 g, 1.27 mmol). The orange solution was heated to 70° C. for 2 hours and 45 minutes. Then the black solution was cooled to ambient temperature (about 23° C.). The solution was filtered and Et$_2$O (1 mL) was added. Concentration to 6 mL led to the formation of a crystalline precipitate. The next day additional Et$_2$O (10 mL) was added. Then the dark crystalline solid was collected on a fritted disk and washed with Et$_2$O (10 mL), then dried under reduced pressure to afford the product as a gray solid. Yield: 40 g, 54%. $^1$H NMR (250 MHz, CD$_2$Cl$_2$): δ 8.00-7.68 (4H, m), 7.37-7.15 (6H, m), 5.15 (2H, m), 3.60 (4H, q), 3.46 (1H, sept), 1.35 (6H, d), 1.16 (6H, d), 1.08 (6H, t).

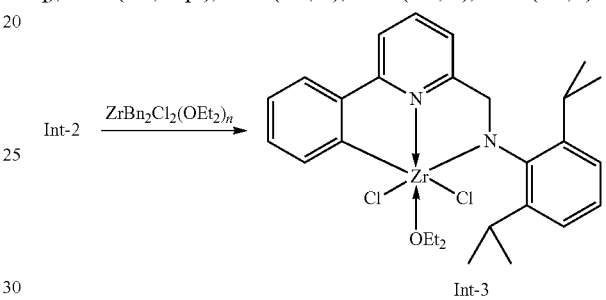

Int-3

Synthesis of Int-4 with Tridentate N—N—C Ligand (not According to Invention)

Int-4 (structure below) is used as intermediate for making N—N—N complexes. Diethyl ether (15 mL) was added to ZrBn$_2$Cl$_2$(OEt$_2$) (0.217 g, 0.519 mmol) to form a cloudy yellow solution. At −68° C. a solution of the imine Int-1 (0.178 g, 0.519 mmol) in Et$_2$O (4 mL) was added dropwise. The mixture was allowed to warm slowly to ambient temperature (about 23° C.) over several hours. After stirring overnight a dark solution had formed. The volatiles were removed by evaporation and the solid was suspended in pentane. The gray solid was collected on a frit, washed with pentane, and then dried under reduced pressure. Yield: 0.24 g, 61%. $^1$H NMR (250 MHz, C$_6$D$_6$): δ 8.22 (1H, d), 6.5-7.3 (ca. 14H, m), 5.88 (1H, d), 4.93 (1H, dd), 4.32 (1H, sept), 3.48 (1H, dd), 3.32 (4H), 2.8-2.1 (2H, m), 1.64 (3H, d), 1.32 (3H, d), 1.28 (3H, d), 1.21 (3H, d), 1.03 (6H, t).

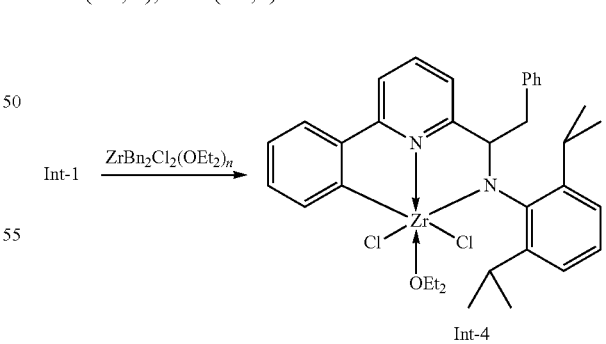

Int-4

Synthesis of Int-5 with Tridentate N—N—C Ligand (not According to Invention)

Int-5 (structure below) is used as intermediate for making N—N—N complexes. Benzene (4 mL) was added to a combination of Int-2 (0.281 g, 0.815 mmol) and HfBn$_2$Cl$_2$(OEt$_2$)$_{1.5}$ (0.442 g, 0.815 mmol). The orange solution was heated to 60° C. for 75 minutes. The volatiles were then evaporated to near dryness. Additional benzene (5 mL) was then added and the suspended solid was collected on a fritted disk, washed with benzene (5 mL), and dried under reduced pressure. Yield: 0.467 g, 86.0%. $^1$H NMR (250 MHz, CD$_2$Cl$_2$): δ 8.00 (1H, t), 7.94 (1H, d), 7.81 (2H, d), 7.40-7.15 (6H, m), 5.40 (2H, s), 3.66 (4H, q), 3.50 (2H, sept), 1.33 (6H, d), 1.17 (6H, d), 1.04 (6H, t).

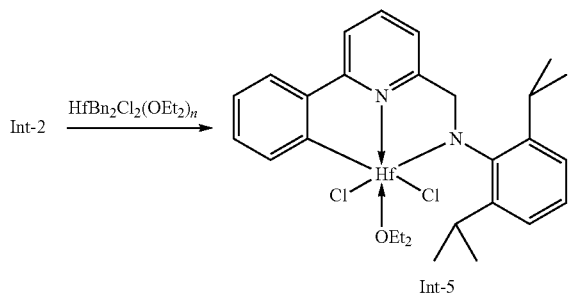

Int-5

Synthesis of Int-6 with Tridentate N—N—C Ligand (not According to Invention)

Int-6 (structure below) is used as intermediate for making N—N—N complexes. Benzene (10 mL) was added to HfBn$_2$Cl$_2$(OEt$_2$)$_{1.5}$ (0.585 g, 1.08 mmol) and the imine Int-1 (0.371 g, 1.08 mmol) to form a dark solution. The mixture was heated to 65° C. for 14 hours and then evaporated to a residue. Et$_2$O (15 mL) was added, and the suspended product was collected on a glass frit, washed with Et$_2$O (5 mL), and dried under reduced pressure. NMR data indicated that about 1.45 equiv of ether was coordinated and/or cocrystallized. Yield: 0.65 g, 76%. $^1$H NMR (250 MHz, CD$_2$Cl$_2$): δ 7.99 (1H, d), 7.80 (2H, t), 7.69 (1H, t), 7.50-7.20 (8H, m), 6.98-6.92 (2H, m), 6.21 (1H, d), 5.09 (1H, dd), 3.98 (1H, sept), 3.52 (5.8H, q), 3.33 (1H, dd), 2.91 (1H, sept), 2.72 (1H, dd), 1.43 (3H, d), 1.28 (3H, d), 1.23 (3H, d), 1.19-1.10 (6H, m).

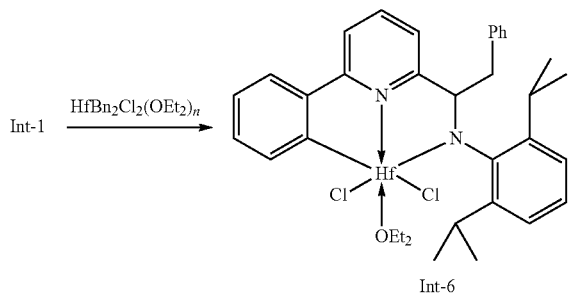

Int-6

Synthesis of Ligand L4 (According to Invention)

Toluene (15 mL) was added to Int-5 (0.0881 g, 0.132 mmol) and PhCH=N(2,5-Me$_2$-C$_6$H$_3$) (0.0277 g, 0.132 mmol). The suspension was warmed to 90° C. to form a clear, pale yellow solution. After 16 hours the volatiles were evaporated, and the residue was dissolved in Et$_2$O (10 mL). Water (10 mL) was then added. The organics were separated, dried over MgSO$_4$, and evaporated to give the diamine product as a thick oil. $^1$H NMR (250 MHz, C$_6$D$_6$): δ 7.55-6.80 (16H, m), 6.62 (1H, s), 6.49 (2H, m), 4.26 (2H, v br), 4.22 (2H, s), 3.45 (2H, sept), 2.03 (3H, s), 1.89 (3H, s), 1.20 (6H, d), 1.17 (6H, d).

Synthesis of C1 with tridentate N—N—N Ligand (According to Invention)

A CH$_2$Cl$_2$ (6 mL) solution of Int-3 (0.101 g, 0.175 mmol) was added to PhCH=NPh (0.0317 g, 0.175 mmol). The vial was sealed and heated to 50° C. for 15.5 hours. The volatiles were removed to afford a residue that was extracted with Et$_2$O (5 mL) and filtered. Concentration of this solution to 1 mL afforded clean product as a yellow crystalline lump. Yield: 0.089 g, 69%. $^1$H NMR data indicates that the crystallized product is a 4:1 mixture of conformational diastereoisomers and has 0.75 equivalents of co-crystallized Et$_2$O. $^1$H NMR (250 MHz, C$_6$D$_6$): δ 7.3-6.6 (overlapping aryls), 6.45 (1.25H, br d), 6.14 (0.25H, d), 5.67 (1H, s), 5.39 (0.22H, s), 4.68 (0.44H, AB quartet, Δν=186 Hz, J=20 Hz), 4.39 (2H, AB quartet, Δν=160 Hz, J=20 Hz), 3.75-3.60 (1.4H, m), 3.26 (3H, q, Et$_2$O), 2.30 (1H, sept), 1.57 (1.62H, dd), 1.50-1.44 (3.86H, m), 1.33 (3.31H, d), 1.11 (5.59H, t), 0.96 (6.28H, d).

Synthesis of C2 with Tridentate N—N—N Ligand (According to Invention)

CH$_2$Cl$_2$ (4 mL) solution of Int-5 (0.105 g, 0.158 mmol) and PhCH=NPh (0.0332 g, 0.183 mmol). The vial was sealed and heated to 60° C. for 18 hours. The volatiles were removed to afford a residue that was dissolved in Et$_2$O (10 mL). Concentration of this solution to 2 mL and leaving overnight caused the excess imine to crystallize. The mother liquor was decanted off. To this was added pentane (4 mL) to cause the product to precipitate as a pale yellow solid. This solid was isolated and dried under reduced pressure. Yield: 0.085 g, 65%. $^1$H NMR data indicates that the product was isolated as a 2:1 mixture of conformational diastereoisomers and that there was a small amount of ether (0.1 equiv) and pentane (0.7 equiv) present. Due to the complexity of the NMR spectrum, only selected (methylidene and methine) resonances are presented. $^1$H NMR (250 MHz, CD$_2$Cl$_2$): δ Major diastereoisomer: 5.71 (1H, s), 4.63 (2H, AB quartet, Δν=97 Hz, J=20 Hz), 3.31 (1H, sept), 1.95 (1H, sept); minor diastereoisomer: 5.89 (1H, s), 5.03 (2H, AB quartet, Δν=221 Hz, J=20 Hz), 3.93 (1H, sept), 3.31 (1H, sept).

Synthesis of C3 with Tridentate N—N—N Ligand (According to Invention)

A CH$_2$Cl$_2$ (6 mL) solution of Int-3 (0.101 g, 0.175 mmol) was added to PhCH=N Pr (0.0269 g, 0.182 mmol). The vial was sealed and heated to 50° C. for 15.5 hours. The volatiles were removed to afford a yellow-orange solid that was extracted with Et$_2$O (5 mL) and filtered. Concentration of this solution to 1 mL afforded clean product as yellow crystals. Yield: 0.079 g, 65%. $^1$H NMR data indicates that the crystallized product is mostly (>90%) a single conformational diastereoisomer and has 0.61 equivalents of co-crystallized Et$_2$O. Due to the complexity of the NMR spectrum, only selected (methylidene and methine) resonances are presented. $^1$H NMR (250 MHz, C$_6$D$_6$): δ 5.33 (1H, sept), 5.32 (1H, s), 4.75 (2H, AB quartet, Δν=152 Hz, J=21 Hz), 4.19 (1H, sept), 3.76 (1H, sept).

Synthesis of C4 with Tridentate N—N—N Ligand (According to Invention)

CH$_2$Cl$_2$ (4 mL) was added to Int-3 (0.089 g, 0.15 mmol) and PhCH=N(2,5-Me$_2$-C$_6$H$_3$) (0.032 g, 0.15 mmol). The vial was sealed and heated to 65° C. overnight. The volatiles were evaporated and the residue was extracted into Et$_2$O (5 mL) and filtered. Concentration of the solution to 1.5 mL afforded the product C4 as crystalline solid overnight. Yield: 0.018 g, 16%. $^1$H NMR data indicates that the product is a complex mixture of conformational diastereoisomers. Reaction of an ether solution of the isolated product with water cleanly formed the diamine L4 (by $^1$H NMR spectroscopy).

Synthesis of C5 with Tridentate N—N—N Ligand (According to Invention)

Toluene (7 mL) and PhCH=N(2,5-Me$_2$-C$_6$H$_3$) (0.0821 g, 0.392 mmol) were combined to form a clear yellow solution. Then this solution was added to solid Int-5 (0.261 g, 0.392 mmol). The mixture was heated to 90° C. overnight. An aliquot of the reaction mixture (about one-third) was filtered and evaporated to afford C5 as a white solid. Yield: 0.114 g, 36.3%. $^1$H NMR data of a CD$_2$Cl$_2$ solution of C5 indicates that the product is a complex mixture of conformational diastereoisomers. The rest of the toluene solution was quenched with water (4 mL). The organics were extracted with Et$_2$O (10 mL), separated, and dried over MgSO$_4$. Filtration and evaporation of the volatiles yielded the diamine L4 (by $^1$H NMR) as a sticky residue. Yield: 0.131 g, 60.3%.

Synthesis of C7 with Tridentate N—N—N Ligand (According to Invention)

A toluene (3 mL) solution of ligand L4 (79.5 mg, 0.144 mmol) was added to solid Zr(NMe$_2$)$_4$ (38.4 mg, 0.144 mmol) to form a yellow solution. The vial was sealed and heated to 120° C. for 1 hour. The volatiles were removed to afford a crystalline residue. This was crystallized from a mixture of toluene (0.5 mL) and hexanes (4 mL) to give the product as colorless crystals. Yield: 70 mg, 67%. $^1$H NMR indicated that a single conformational diastereoisomer was present. $^1$H NMR (250 MHz, CD$_2$Cl$_2$): δ 7.5-6.6 (18H), 5.24 (1H, s), 4.93 (2H, AB quartet, Δv=146 Hz, J=20 Hz), 3.91 (1H, sept), 3.53 (1H, sept), 2.44 (3H, s), 2.19 (6H, s), 2.09 (3H, s), 1.88 (6H, s), 1.50 (3H, d), 1.4-0.8 (18H, overlapping multiplets and some co-crystallized hexanes). The identity of the product was confirmed by single-crystal X-ray diffraction.

Synthesis of C8 with N—N—N Ligand (According to Invention) by Salt-Metathesis

Benzene (4 mL) was added to complex C1 (111 mg, 0.147 mmol) to form a suspension. Then an Et$_2$O solution of Me$_2$Mg (0.94 mL, 0.163 mmol) was added drop-wise over a 2 to 3 minutes. After 30 minutes the volatiles were evaporated and the residue was extracted with benzene (4 mL). The solution was filtered and evaporated under reduced pressure to yield the product as a foam. Yield: 93 mg, 98%. $^1$H NMR data indicates that the product is a 3:2 mixture of conformational diastereoisomers. Due to the complexity of the spectrum only selected resonances for each diastereoisomer are presented. $^1$H NMR (250 MHz, C$_6$D$_6$): 6 major diastereoisomer: 5.79 (1H, s), 4.49 (2H, AB quartet, Δv=155 Hz, J=20 Hz), 0.64 (3H, s, Zr-Me), 0.06 (3H, s, Zr-Me); minor diastereoisomer: 5.79 (1H, s), 4.89 (2H, AB quartet, Δv=134 Hz, J=20 Hz), 0.23 (3H, s, Zr-Me), −0.16 (3H, s, Zr-Me).

Polymerizations Examples

General Polymerization Procedures

Ethylene/1-octene copolymerizations were carried out in a parallel, pressure reactor, as generally described in U.S. Pat. No. 6,306,658; U.S. Pat. No. 6,455,316; U.S. Pat. No. 6,489,168; WO 00/09255; and Murphy et al., J. Am. Chem. Soc., 2003, 125, pages 4306-4317, each of which is fully incorporated herein by reference for US purposes. A pre-weighed glass vial insert and disposable stirring paddle were fitted to each reaction vessel of the reactor, which contains 48 individual reaction vessels. The reactor was then closed and each vessel was individually heated to a set temperature (usually between 50 and 110° C.) and pressurized to a predetermined pressure of 1.38 MPa (200 psi) ethylene. 1-Octene (100 microliters, 637 micromol) was injected into each reaction vessel through a valve, followed by enough toluene to bring the total reaction volume, including the subsequent additions, to 5 mL. Tri-n-octylaluminum in toluene (100 microliters, 10 mM in toluene, 1 micromol) was then added to act as a co-catalyst/scavenger, if used. The pyridylamido catalyst Int-3 is not according to the invention; catalysts C1, C3, and C8 are.

The contents of the vessel were then stirred at 800 rpm. An activator solution (either 1.0 equiv of 0.40 mM dimethyl anilinium tetrakis-pentafluorophenyl borate (dmah-NCA) in toluene or 100-1000 mol equiv of methyl alumoxane (MAO) in toluene) was then injected into the reaction vessel along with 500 microliters toluene, followed by a toluene solution of catalyst (0.40 mM in toluene, between 20-40 nanomols of catalyst and another aliquot of toluene (500 microliters). Equivalence is determined based on the mol equivalents relative to the moles of the transition metal in the catalyst complex.

The reaction was then allowed to proceed until 20 psi ethylene had been taken up by the reaction (ethylene pressure was maintained in each reaction vessel at the pre-set level by computer control). At this point, the reaction was quenched by pressurizing the vessel with compressed air. After the polymerization reaction, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight, by FT-IR (see below) to determine comonomer incorporation, and by DSC (see below) to determine melting point.

To determine various molecular weight related values by GPC, high temperature size exclusion chromatography was performed using an automated "Rapid GPC" system as generally described in U.S. Pat. No. 6,491,816; U.S. Pat. No. 6,491,823; U.S. Pat. No. 6,475,391; U.S. Pat. No. 6,461,515; U.S. Pat. No. 6,436,292; U.S. Pat. No. 6,406,632; U.S. Pat. No. 6,175,409; U.S. Pat. No. 6,454,947; U.S. Pat. No. 6,260,407; and U.S. Pat. No. 6,294,388; each of which is fully incorporated herein by reference for US purposes. This apparatus has a series of three 30 cm×7.5 mm linear columns, each containing PLgel 10 um, Mix B. The GPC system was calibrated using polystyrene standards ranging from 580-3,390,000 g/mol. The system was operated at an eluent flow rate of 2.0 mL/min and an oven temperature of 165° C. 1,2,4-trichlorobenzene was used as the eluent. The polymer samples were dissolved in 1,2,4-trichlorobenzene at a concentration of 0.1-0.9 mg/mL. 250 uL of a polymer solution was injected into the system. The concentration of the polymer in the eluent was monitored using an evaporative light scattering detector. The molecular weights presented are relative to linear polystyrene standards.

Differential Scanning Calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./min and then cooled at a rate of 50° C./min. Melting points were collected during the heating period. The ratio of 1-octene to ethylene incorporated in the polymers (weight %) was determined by rapid FT-IR spectroscopy on a Bruker Equinox 55+ IR in reflection mode. Samples were prepared in a thin film format by evaporative deposition techniques. Weight percent 1-octene was obtained from the ratio of peak heights at 1378 and 4322 cm$^{-1}$. This method was calibrated using a set of ethylene/1-octene copolymers with a range of known wt % 1-octene content.

Example 1

Polymerization of Ethylene and 1-octene Mixture Using Int-3 and C1

The polymerizations were performed in a parallel pressure reactor as described above, but with the following specifics. MAO activator (1000 equivalents per catalyst equivalent) was added as a 1 wt % toluene solution. Catalyst concentrations were 0.00800 mM (40 nanomols catalyst used). Trialkyl aluminum scavengers were not used. Data are shown in Table 1. Catalyst C1 is formed by the reaction of PhCH═NPh with Int-3. The data shown indicates that C1 has a greater activity for the formation of ethylene-octene copolymers than does Int-3 at temperatures between 50 and 100° C. The C1 catalyst also generally forms lower molecular weight polymer (than does Int-3) that has lower $M_w/M_n$ values. Catalyst Int-3 is not according to the invention; catalyst C1 is according to the invention.

TABLE 1

Polymerization of ethylene and 1-octene using Int-3 and C1.

| Example | catalyst | activator (1000 equiv) | Temp (° C.) | activity (g/mmol cat/h/bar) | wt % octene | $M_w$ | $M_n$ | $M_w/M_n$ |
|---|---|---|---|---|---|---|---|---|
| 1 | Int-3 | MAO | 50 | 5076 | 4 | 450,668 | 97,606 | 4.6 |
| 2 | Int-3 | MAO | 80 | 15626 | 4 | 180,608 | 53,629 | 3.4 |
| 3 | Int-3 | MAO | 80 | 14607 | 5 | 252,141 | 77,375 | 3.3 |
| 4 | Int-3 | MAO | 110 | 18076 | 4 | 132,804 | 48,142 | 2.8 |
| 5 | Int-3 | MAO | 110 | 20210 | 3 | 129,407 | 48,292 | 2.7 |
| 6 | C1 | MAO | 50 | 29207 | 3 | 133,973 | 60,086 | 2.2 |
| 7 | C1 | MAO | 50 | 25620 | 3 | 110,680 | 50,435 | 2.2 |
| 8 | C1 | MAO | 80 | 46641 | 5 | 72,715 | 37,599 | 1.9 |
| 9 | C1 | MAO | 80 | 42145 | 4 | 74,381 | 40,141 | 1.9 |
| 10 | C1 | MAO | 110 | 30894 | 5 | 55,531 | 23,382 | 2.4 |
| 11 | C1 | MAO | 110 | 31797 | 3 | 59,355 | 26,909 | 2.2 |

Example 2

Polymerization of Ethylene and 1-Octene Mixture Using Int-3 and C3

The polymerizations were performed in a parallel pressure reactor as described above, but with the following specifics. MAO activator (1000 equivalents per catalyst equivalent) was added as a 1 wt % toluene solution. Catalyst concentrations were 0.00800 mM (40 nanomols catalyst used). Trialkyl aluminum scavengers were not used. Data are shown in Table 2. Catalyst C3 is formed by the reaction of PhCH=N$^i$Pr with catalyst Int-3. The data shown indicates that C3 has a greater activity for the formation of ethylene-octene copolymers than does Int-3 at 50° C., but is less active at higher temperatures. Catalyst Int-3 is not according to the invention; catalyst C3 is according to the invention.

TABLE 2

Polymerization of ethylene and 1-octene using Int-3 and C3.

| example | catalyst | activator (1000 equiv) | Temp (° C.) | activity (g/mmol cat/h/bar) | wt % octene | $M_w$ | $M_n$ | $M_w/M_n$ |
|---|---|---|---|---|---|---|---|---|
| 1 | Int-3 | MAO | 50 | 5076 | 4 | 450,668 | 97,606 | 4.6 |
| 2 | Int-3 | MAO | 80 | 15626 | 4 | 180,608 | 53,629 | 3.4 |
| 3 | Int-3 | MAO | 80 | 14607 | 5 | 252,141 | 77,375 | 3.3 |
| 4 | Int-3 | MAO | 110 | 18076 | 4 | 132,804 | 48,142 | 2.8 |
| 5 | Int-3 | MAO | 110 | 20210 | 3 | 129,407 | 48,292 | 2.7 |
| 6 | C3 | MAO | 50 | 14125 | 3 | 184,000 | 94,143 | 2.0 |
| 7 | C3 | MAO | 50 | 20104 | 2 | 188,145 | 102,570 | 1.8 |
| 8 | C3 | MAO | 80 | 5887 | 3 | 163,568 | 75,673 | 2.2 |
| 9 | C3 | MAO | 80 | 5128 | 2 | 142,768 | 73,769 | 1.9 |
| 10 | C3 | MAO | 110 | 1224 | 3 | 129,461 | 30,544 | 4.2 |
| 11 | C3 | MAO | 110 | 829 | 3 | 125,633 | 31,788 | 4.0 |

Example 3

Polymerization of Ethylene and 1-Octene Mixture Using C8

The polymerizations were performed in the parallel pressure reactor as described above, but with the following specifics. Isohexane was used as the solvent. N,N-Dimethylanilinium tetrakis(pentafluorophenyl)borate, abbreviated as dmah-NCA, activator (1.0 equivalents per catalyst equivalent) was added as a 20 mM toluene solution. Catalyst concentrations were 0.00400 mM (20 nanomols catalyst used). Tri-n-octylaluminum (0.100 mL of 0.010 M solution in isohexane) was used as a scavenger. Data are shown in Table 3. The data shown indicate that C8 with the non-coordinating anion activator dmah-NCA is an active catalyst for the polymerization of an ethylene 1-octene mixture.

TABLE 3

Polymerization of ethylene and 1-octene using C8.

| example | catalyst | activator (1.0 equiv) | T (° C.) | activity (g/mmol cat/h/bar) | $M_w$ | $M_n$ | $M_w/M_n$ |
|---|---|---|---|---|---|---|---|
| 1 | C8 | dmah-NCA | 50 | 14034 | 630778 | 338252 | 630778 |
| 2 | C8 | dmah-NCA | 80 | 22582 | 544394 | 283986 | 544394 |
| 3 | C8 | dmah-NCA | 80 | 22197 | 492637 | 262243 | 492637 |
| 4 | C8 | dmah-NCA | 110 | 157 | 337119 | 175278 | 337119 |
| 5 | C8 | dmah-NCA | 110 | 182 | 369850 | 174061 | 369850 |

Example 4

Polymerization of Propylene Using C1-C2, C3 and C5

The polymerizations were performed in a parallel pressure reactor in a manner analogous to that described above for ethylene-octene polymerizations, but with the following specifics. Isohexane was used as the solvent. Propylene (1.0 mL) was used instead of 1-octene. The total volume was 5.10 mL. MAO activator (700 equivalents per catalyst equivalent) was added as a 1 wt % toluene solution. Catalyst concentrations were 0.01600 mM (80 nanomols catalyst used). Trialkyl aluminum scavengers were not used. Reactions were allowed to proceed for 20 minutes. Data are shown in Table 4. The data shown indicate that the pyridyldiamido complexes C1, C2, C3, and C5 with MAO activator are active catalysts for the polymerization of propylene.

TABLE 4

Polymerization of propylene using C1, C2, C3, and C5.

| example | catalyst | activator (700 Equiv) | T (° C.) | activity (g/mmol cat/hr) | $M_w$ | $M_n$ | $M_w/M_n$ |
|---|---|---|---|---|---|---|---|
| 1 | C1 | MAO | 70 | 4961 | 25962 | 11153 | 2.3 |
| 2 | C1 | MAO | 70 | 5133 | 26942 | 11876 | 2.3 |
| 3 | C1 | MAO | 85 | 2155 | 14837 | 6731 | 2.2 |
| 4 | C1 | MAO | 85 | 2216 | 15834 | 7051 | 2.2 |
| 5 | C1 | MAO | 100 | 1089 | 9231 | 4465 | 2.1 |
| 6 | C1 | MAO | 100 | 981 | 7954 | 4121 | 1.9 |
| 7 | C2 | MAO | 70 | 3780 | 19399 | 8710 | 2.2 |
| 8 | C2 | MAO | 70 | 3891 | 19649 | 8669 | 2.3 |
| 9 | C2 | MAO | 85 | 2297 | 7941 | 4190 | 1.9 |
| 10 | C2 | MAO | 85 | 2388 | 8549 | 4480 | 1.9 |
| 11 | C2 | MAO | 100 | 2644 | 28432 | 4495 | 6.3 |
| 12 | C2 | MAO | 100 | 2508 | 27754 | 4385 | 6.3 |
| 13 | C3 | MAO | 70 | 1780 | 10548 | 5534 | 1.9 |
| 14 | C3 | MAO | 70 | 3158 | 77692 | 10657 | 7.3 |
| 15 | C3 | MAO | 85 | 1435 | 8698 | 4618 | 1.9 |
| 16 | C3 | MAO | 85 | 1453 | 10089 | 5092 | 2 |
| 17 | C3 | MAO | 100 | 857 | 5636 | 3388 | 1.7 |
| 18 | C3 | MAO | 100 | 889 | 5870 | 3500 | 1.7 |
| 19 | C5 | MAO | 70 | 3462 | 59630 | 12391 | 4.8 |
| 20 | C5 | MAO | 70 | 2369 | 18887 | 7990 | 2.4 |
| 21 | C5 | MAO | 85 | 2377 | 21442 | 8483 | 2.5 |
| 22 | C5 | MAO | 85 | 3726 | 45757 | 13980 | 3.3 |
| 23 | C5 | MAO | 100 | 2321 | 14701 | 6458 | 2.3 |
| 24 | C5 | MAO | 100 | 2315 | 14819 | 6514 | 2.3 |

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What is claimed is:

1. A pyridyldiamido transition metal complex having the general formula: (I)

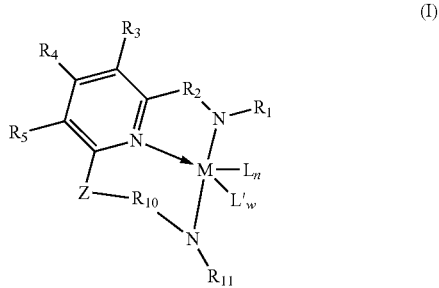

wherein:
M is a Group 3, 4, 5, 6, 7, 8, 9, 10, 11 or 12 metal;
Z is

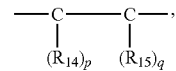

where $R_{14}$ and $R_{15}$ are independently selected from the group consisting of hydrogen, hydrocarbyls, and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings, p is 1 or 2, and q is 1 or 2;

$R_1$ and $R_{11}$ are independently selected from the group consisting of hydrocarbyls, and substituted hydrocarbyls, or silyl groups;

$R_2$ and $R_{10}$ are each, independently, -E($R_{12}$)($R_{13}$)— with E being carbon, silicon, or germanium, and each $R_{12}$ and $R_{13}$ being independently selected from the group consisting of hydrogen, hydrocarbyls, and substituted hydrocarbyls, alkoxy, silyl, amino, aryloxy, halogen, and phosphino, $R_{12}$ and $R_{13}$ may be joined to form a saturated, substituted or unsubstituted hydrocarbyl ring, where the ring has 4, 5, 6, or 7 ring carbon atoms and where substitutions on the ring join to form additional rings, or $R_{12}$ and $R_{13}$ may be joined to form a saturated heterocyclic ring, or a saturated substituted heterocyclic ring where substitutions on the ring can join to form additional rings;

$R_3$, $R_4$, and $R_5$ are independently selected from the group consisting of hydrogen, hydrocarbyls, substituted hydrocarbyls, alkoxy, aryloxy, halogen, amino, and silyl, and wherein adjacent R groups $R_3$ and $R_4$ and/or adjacent R groups $R_4$ and $R_5$ may be joined to form a substituted or unsubstituted hydrocarbyl or heterocyclic ring, where the ring has 5, 6, 7, or 8 ring atoms and where substitutions on the ring can join to form additional rings;
L is an anionic leaving group, where the L groups may be the same or different and any two L groups may be linked to form a dianionic leaving group;
n is 0, 1, 2, 3, or 4;
L' is neutral Lewis base; and
w is 0, 1, 2, 3, or 4.

2. The complex of claim 1 wherein M is Ti, Zr, or Hf, and/or Z is a substituted aryl group bridging the $NR_{11}$ moiety to the remainder of the complex by a chain of three adjacent atoms of which two are adjacent carbons of a substituted phenyl ring and the third is covalently bonded to one of these two carbons.

3. The complex of claim 1 wherein $R_2$ and $R_{10}$ are each, independently, represented by the formula:

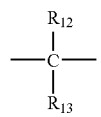

where $R_{12}$ is hydrogen, alkyl, aryl, or halogen, and $R_{13}$ is hydrogen, alkyl, aryl, or halogen.

4. The complex of claim 1 wherein the complex is of the general formula (IV):

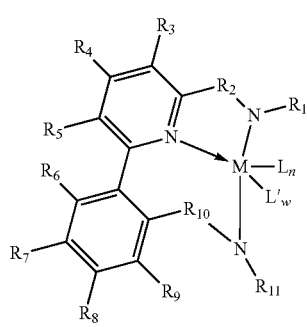

(IV)

wherein
$R_6$, $R_7$, $R_8$, and $R_9$ are independently selected from the group consisting of hydrogen, hydrocarbyls, substituted hydrocarbyls, alkoxy, halogen, amino, and silyl, and wherein adjacent R groups $R_6$ and $R_7$ and/or adjacent R groups $R_7$ and $R_8$ and/or adjacent R groups $R_8$ and $R_9$ may be joined to form a saturated, substituted or unsubstituted hydrocarbyl or heterocyclic ring, where the ring has 5, 6, 7, or 8 ring carbon atoms and where substitutions on the ring can join to form additional rings; and M, L, L', w, n, $R_1$, $R_2$, $R_3$, $R_4$, $R_5$, $R_{10}$, and $R_{11}$ are as defined in claim 1.

5. The complex of claim 1 wherein $R_1$, $R_3$, $R_4$, $R_5$, $R_{11}$, $R_{12}$, $R_{13}$, $R_{14}$, and $R_{15}$ each contain no more than 30 carbon atoms.

6. The complex of claim 4 wherein $R_1$, $R_3$, $R_4$, $R_5$, $R_6$, $R_7$, $R_8$, $R_9$, $R_{11}$, $R_{12}$, $R_{13}$, $R_{14}$, and $R_{15}$ each contain no more than 30 carbon atoms.

7. The complex of claim 1 wherein E is carbon and $R_1$ and $R_{11}$ are independently selected from phenyl groups that are substituted with 0, 1, 2, 3, 4 or 5 substituents selected from the group consisting of F, Cl, Br, I, $CF_3$, $NO_2$, alkoxy, dialkylamino, hydrocarbyl, and substituted hydrocarbyl groups with from one to ten carbons.

8. The complex of claim 1 wherein each L is independently selected from the group consisting of halide, alkyl, aryl, alkoxy, amido, hydrido, phenoxy, hydroxy, silyl, allyl, alkenyl, and alkynyl.

9. The complex of claim 1 wherein each L' is independently selected from the group consisting of ethers, thio-ethers, amines, nitriles, imines, pyridines, and phosphines.

10. A process for preparing the pyridyldiamido complex of claim 1 comprising the insertion of an imine into the metal-carbon bond of an ortho-metalated aryl group of a separately synthesized intermediate pyridylamido metal complex as shown in equation (V):

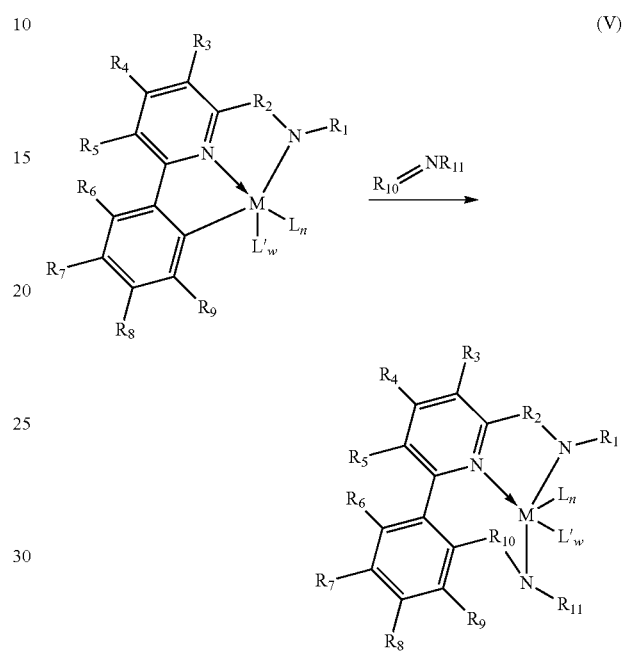

(V)

wherein M, L, L', w, n, $R_1$, $R_2$, $R_3$, $R_4$, $R_5$, $R_{10}$, and $R_{11}$ are as defined in claim 1, and $R_6$, $R_7$, $R_8$, and $R_9$ are independently selected from the group consisting of hydrogen, hydrocarbyls, substituted hydrocarbyls, alkoxy, halogen, amino, and silyl, and wherein adjacent R groups $R_6$ and $R_7$ and/or adjacent R groups $R_7$ and $R_8$ and/or adjacent R groups $R_8$ and $R_9$ may be joined to form a saturated, substituted or unsubstituted hydrocarbyl or heterocyclic ring, where the ring has 5, 6, 7, or 8 ring carbon atoms and where substitutions on the ring can join to form additional rings.

11. A catalyst system comprising an activator and a pyridyldiamido transition metal complex having the general formula (I):

(I)

wherein:
M is a Group 3, 4, 5, 6, 7, 8, 9, 10, 11, or 12 metal;
Z is $$-\underset{(R_{14})_p}{C}-\underset{(R_{15})_q}{C}-,$$

where $R_{14}$ and $R_{15}$ are independently selected from the group consisting of hydrogen, hydrocarbyls, and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings, p is 1 or 2, and q is 1 or 2;

$R_1$ and $R_{11}$ are independently selected from the group consisting of hydrocarbyls, substituted hydrocarbyls, and silyl groups;

$R_2$ and $R_{10}$ are each, independently, -E($R_{12}$)($R_{13}$)— with E being carbon, silicon, or germanium, and each $R_{12}$ and $R_{13}$ being independently selected from the group consisting of hydrogen, hydrocarbyls, substituted hydrocarbyls, alkoxy, silyl, amino, aryloxy, halogen, and phosphino, $R_{12}$ and $R_{13}$ may be joined to form a saturated, substituted or unsubstituted hydrocarbyl ring, where the ring has 4, 5, 6, or 7 ring carbon atoms and where substitutions on the ring can join to form additional rings, or $R_{12}$ and $R_{13}$ may be joined to form a saturated heterocyclic ring, or a saturated substituted heterocyclic ring where substitutions on the ring can join to form additional rings;

$R_3$, $R_4$, and $R_5$ are independently selected from the group consisting of hydrogen, hydrocarbyls, substituted hydrocarbyls, alkoxy, aryloxy, halogen, amino, and silyl, and wherein adjacent R groups $R_3$ and $R_4$ and/or adjacent R groups $R_4$ and $R_5$ may be joined to form a substituted or unsubstituted hydrocarbyl or heterocyclic ring, where the ring has 5, 6, 7, or 8 ring atoms and where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base; and w is 0, 1, 2, 3, or 4.

12. The catalyst system of claim 11 wherein the activator is an alumoxane.

13. The catalyst system of claim 11 wherein the activator is a non-coordinating anion.

14. A polymerization process comprising a) contacting one or more alkene monomers with a catalyst system comprising: i) an activator and ii) a pyridyldiamido transition metal complex having the general formula (I):

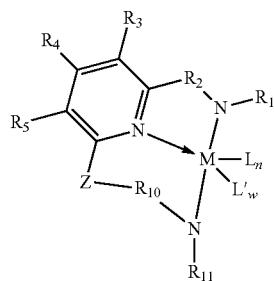

(I)

wherein:

M is a Group 3, 4, 5, 6, 7, 8, 9, 10, 11, or 12 metal;

Z is

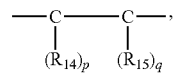

where $R_{14}$ and $R_{15}$ are independently selected from the group consisting of hydrogen, hydrocarbyls, and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings, p is 1 or 2, and q is 1 or 2;

$R_1$ and $R_{11}$ are independently selected from the group consisting of hydrocarbyls, substituted hydrocarbyls, and silyl groups;

$R_2$ and $R_{10}$ are each, independently, -E($R_{12}$)($R_{13}$)— with E being carbon, silicon, or germanium, and each $R_{12}$ and $R_{13}$ being independently selected from the group consisting of hydrogen, hydrocarbyls, substituted hydrocarbyls, alkoxy, silyl, amino, aryloxy, halogen, and phosphino, $R_{12}$ and $R_{13}$ may be joined to form a saturated, substituted or unsubstituted hydrocarbyl ring, where the ring has 4, 5, 6, or 7 ring carbon atoms and where substitutions on the ring can join to form additional rings, or $R_{12}$ and $R_{13}$ may be joined to form a saturated heterocyclic ring, or a saturated substituted heterocyclic ring where substitutions on the ring can join to form additional rings;

$R_3$, $R_4$, and $R_5$ are independently selected from the group consisting of hydrogen, hydrocarbyls, substituted hydrocarbyls, alkoxy, aryloxy, halogen, amino, and silyl, and wherein adjacent R groups $R_3$ and $R_4$ and/or adjacent R groups $R_4$ and $R_5$ may be joined to form a substituted or unsubstituted hydrocarbyl or heterocyclic ring, where the ring has 5, 6, 7, or 8 ring atoms and where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base; and w is 0, 1, 2, 3, or 4; and b) obtaining polymer.

15. The process of claim 14 wherein the activator is an alumoxane.

16. The process of claim 14 wherein the monomer comprises ethylene.

17. The process of claim 14 wherein the monomer comprises propylene.

18. The process of claim 14 wherein the pyridyldiamido transition metal complex is supported.

19. The process of claim 14 wherein the complex is of the general formula (IV):

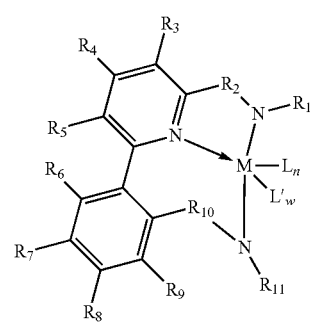

(IV)

wherein R$_6$, R$_7$, R$_8$, and R$_9$ are independently selected from the group consisting of hydrogen, hydrocarbyls, substituted hydrocarbyls, alkoxy, halogen, amino, and silyl, and wherein adjacent R groups R$_6$ and R$_7$ and/or adjacent R groups R$_7$ and R$_8$ and/or adjacent R groups R$_8$ and R$_9$ may be joined to form a saturated, substituted or unsubstituted hydrocarbyl or heterocyclic ring, where the ring has 5, 6, 7, or 8 ring carbon atoms and where substitutions on the ring can join to form additional rings; and M, L, L', w, n, R$_1$, R$_2$, R$_3$, R$_4$, R$_5$, R$_{10}$, and R$_{11}$ are as defined in claim 14.

20. The process of claim 14 wherein the activator is a non-coordinating anion.